US010639015B2

(12) United States Patent
Heikenfeld

(10) Patent No.: US 10,639,015 B2
(45) Date of Patent: May 5, 2020

(54) DEVICES WITH REDUCED SWEAT VOLUMES BETWEEN SENSORS AND SWEAT GLANDS

(71) Applicant: University of Cincinnati, Cincinnati, OH (US)

(72) Inventor: Jason C. Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 731 days.

(21) Appl. No.: 15/314,418

(22) PCT Filed: May 28, 2015

(86) PCT No.: PCT/US2015/032893
§ 371 (c)(1),
(2) Date: Nov. 28, 2016

(87) PCT Pub. No.: WO2015/184097
PCT Pub. Date: Dec. 3, 2015

(65) Prior Publication Data
US 2017/0095233 A1 Apr. 6, 2017

Related U.S. Application Data

(60) Provisional application No. 62/003,675, filed on May 28, 2014, provisional application No. 62/003,715, (Continued)

(51) Int. Cl.
A61B 5/00 (2006.01)
A61B 10/00 (2006.01)
(Continued)

(52) U.S. Cl.
CPC ........ *A61B 10/0064* (2013.01); *A61B 5/0531* (2013.01); *A61B 5/0537* (2013.01);
(Continued)

(58) Field of Classification Search
CPC ........... A61B 10/00; A61B 5/00; A61B 5/053; A61B 5/145; A61B 5/0531; A61B 5/4266;
(Continued)

(56) References Cited

U.S. PATENT DOCUMENTS

| 4,190,060 A | 2/1980 | Greenleaf et al. |
| 4,542,751 A | 9/1985 | Webster et al. |

(Continued)

FOREIGN PATENT DOCUMENTS

| CA | 2869469 A1 | 10/2013 |
| CN | 101489470 A | 7/2009 |

(Continued)

OTHER PUBLICATIONS

International Searching Authority, Search Report and Written Opinion issued in related International Application No. PCT/US2017/013453 dated May 18, 2017, 14 pages.

(Continued)

*Primary Examiner* — Eric J Messersmith
(74) *Attorney, Agent, or Firm* — Wood Herron & Evans LLP

(57) ABSTRACT

A sweat sensor device (400c) for sensing sweat on the skin (12) includes one or more sweat sensors (420) and a volume-reducing component that provides a volume-reduced pathway (480) for sweat between the one or more sweat sensors (420) and sweat glands in said skin (12) when the device (400c) is positioned on said skin (12). The volume-reducing component may include a volume-reducing material (470) and a pressure-permeated component (460), a sweat dissolvable material (490), a mechanically compliant material (570) for conforming to the skin (12), an adhesive with a vertically anisotropic sweat pathway, and microcapsules (1385) including a barrier material. The presence of a volume- (Continued)

reducing component reduces the sweat volume and decreases the sampling interval.

24 Claims, 12 Drawing Sheets

Related U.S. Application Data filed on May 28, 2014, provisional application No. 62/003,692, filed on May 28, 2014, provisional application No. 62/074,295, filed on Nov. 3, 2014, provisional application No. 62/114,835, filed on Feb. 11, 2015, provisional application No. 62/141,327, filed on Apr. 1, 2015.

(51) Int. Cl.
   *A61B 5/053*      (2006.01)
   *A61B 5/145*      (2006.01)

(52) U.S. Cl.
   CPC ........ *A61B 5/14521* (2013.01); *A61B 5/4266* (2013.01); *A61B 5/6833* (2013.01); *A61B 2560/0412* (2013.01)

(58) Field of Classification Search
   CPC . A61B 5/0537; A61B 5/6833; A61B 10/0064; A61B 5/14521; A61B 2560/0412
   See application file for complete search history.

(56) References Cited

U.S. PATENT DOCUMENTS

| | | | |
|---|---|---|---|
| 4,756,314 A | 7/1988 | Eckenhoff et al. | |
| 4,820,263 A | 4/1989 | Spevak et al. | |
| 5,036,861 A | 8/1991 | Sembrowich et al. | |
| 5,050,604 A | 9/1991 | Reshef et al. | |
| 5,140,985 A | 8/1992 | Schroeder et al. | |
| 5,246,003 A | 9/1993 | DeLonzor | |
| 5,438,984 A | 8/1995 | Schoendorfer | |
| 5,556,789 A | 9/1996 | Goerlach-Graw et al. | |
| 5,599,283 A * | 2/1997 | Lindenmeyer | A61F 5/01 602/20 |
| 5,814,599 A | 9/1998 | Mitragotri et al. | |
| 5,944,662 A | 8/1999 | Schoendorter | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,592,529 B2 | 7/2003 | Marett | |
| 6,666,821 B2 | 12/2003 | Keimel | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 * | 11/2006 | Edmonson | A61B 5/14521 600/346 |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 * | 3/2010 | Potts | A61B 5/14521 600/346 |
| 2010/0130843 A1 | 5/2010 | Caceres Galvez et al. | |
| 2010/0132485 A1 | 6/2010 | Erez et al. | |
| 2010/0198521 A1 | 8/2010 | Haick | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0257064 A1 * | 9/2014 | Einck | A61B 5/4266 600/346 |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen | |
| 2015/0112164 A1 | 4/2015 | Heikenfeld et al. | |
| 2015/0112165 A1 | 4/2015 | Heikenfeld | |
| 2016/0058354 A1 | 3/2016 | Phan et al. | |
| 2016/0066828 A1 | 3/2016 | Phan et al. | |
| 2016/0157768 A1 | 6/2016 | Braig et al. | |

FOREIGN PATENT DOCUMENTS

| | | | |
|---|---|---|---|
| EP | 0282349 | A2 | 9/1988 |
| EP | 0453283 | A1 | 10/1991 |
| EP | 0634215 | A1 | 1/1995 |
| EP | 1500937 | A1 | 1/2005 |
| EP | 1637889 | A1 | 3/2006 |
| EP | 2551784 | A1 | 1/2013 |
| JP | H07-77525 | A | 3/1995 |

(56) References Cited

FOREIGN PATENT DOCUMENTS

| | | |
|---|---|---|
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009052321 A2 | 4/2009 |
| WO | 2010/017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |

OTHER PUBLICATIONS

International Searching Authority, Search Report and Written Opinion issued in related International Application No. PCT/US2017/039421 dated Sep. 6, 2017, 10 pages.
International Searching Authority, Search Report and Written Opinion issued in related International Application No. PCT/US2017/040588 dated Sep. 25, 2017, 11 pages.
Australian Patent Office, Patent Examination Report No. 1 issued in Australian Application No. 2013243541 dated Nov. 25, 2016, 4 pages.
Australian Patent Office, Notice of Acceptance for Patent Application issued in Australian Application No. 2013243541 dated Mar. 23, 2017 (3 pages).
Chinese Patent Office, First Office Action issued in Chinese Application No. 201380028053.8 dated Dec. 21, 2015, 4 pages.
Chinese Patent Office, Second Office Action issued in Chinese Application No. 201380028053.8 dated Sep. 20, 2016, 8 pages (including English language translation).
Chinese Patent Office, Third Office Action issued in Chinese Application No. 201380028053.8 dated Mar. 20, 2017, 17 pages (including English language translation).
European Patent Office, Written Opinion of the International Searching Authority / International Preliminary Report on Patentability dated Oct. 16, 2014 (14 pages).
European Patent Office, Partial European Search Report issued in European Application No. 16203346.8-1657 dated Mar. 24, 2017, 7 pages.
Fu et al., "Controlled Reagent Transport in Disposable 2D Paper Networks", The Royal Society of Chemistry 2010, Lab Chip, 2010, 10, 918-920.
International Bureau, Notification Concerning Transmittal of International Preliminary Report on Patentability issued in International Application No. PCT/US13/35092 dated Oct. 7, 2014, 14 pages.
International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.

International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.
International Searching Authority, Search Report and Written Opinion issued in International Application No. PCT/US2014/061098 dated Dec. 19, 2014, 13 pages.
International Searching Authority, Search Report and Written Opinion issued in International Application No. PCT/US2014/061083 dated Mar. 31, 2015, 18 pages.
International Searching Authority, Search Report and Written Opinion issued in International Application No. PCT/US2015/032830 dated Aug. 14, 2015, 9 pages.
International Searching Authority, Search Report and Written Opinion issued in International Application No. PCT/US2015/032843 dated Oct. 26, 2015, 11 pages.
International Searching Authority, Search Report and Written Opinion issued in International Application No. PCT/US2015/032893 dated Nov. 13, 2015, 14 pages.
International Searching Authority, Search Report and Written Opinion issued in International Application No. PCT/US2015/032866 dated Nov. 19, 2015, 12 pages.
International Searching Authority, Search Report and Written Opinion issued in International Application No. PCT/US2015/051439 dated Dec. 28, 2015, 7 pages.
International Searching Authority, Search Report and Written Opinion issued in International Application No. PCT/US2015/040113 dated Feb. 4, 2016, 13 pages.
International Searching Authority, Search Report and Written Opinion issued in International Application No. PCT/US16/18635 dated May 6, 2016, 12 pages.
International Searching Authority, Search Report and Written Opinion issued in International Application No. PCT/US16/17726 dated May 12, 2016, 9 pages.
International Searching Authority, Search Report and Written Opinion issued in International Application No. PCT/US16/50928 dated Sep. 9, 2016, 8 pages.
International Searching Authority, Search Report and Written Opinion issued in International Application No. PCT/US16/43862 dated Oct. 19, 2016, 14 pages.
International Searching Authority, Search Report and Written Opinion issued in International Application No. PCT/US16/59392 dated Oct. 28, 2016, 13 pages.
Japanese Patent Office, Office Action issued in Japanese Application No. 2015-504702 dated Jan. 20, 2017, 7 pages. (including English language translation).
Stoppa, Matteo, et. al., "Wearable Electronics and Smart Tectiles: A Critical Review," Sensors, 2014, pp. 11957-11992, vol. 14 (36 pages).
European Patent Office, Supplemental European Search Report issued in European Application No. 15799514.3-1657 dated Dec. 7, 2017, 8 pages.

(56) References Cited

OTHER PUBLICATIONS

European Patent Office, Supplemental European Search Report issued in European Application No. 15799317.1-1657 dated Dec. 21, 2017, 9 pages.
European Patent Office, Partial European Search Report issued in European Application No. 15800043.0-115 dated Jan. 8, 2018, 13 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages.
European Patent Office, Official Communication for EP Application No. 13 718 933.8-1101 dated Feb. 14, 2018 (5 pages).
European Patent Office, Extended European Search Report issued in European Application No. 15819306.0-1115 dated Feb. 9, 2018 (9 pages).
International Searching Authority, Search Report and Written Opinion issued in International Application No. PCT/US2017/067495 dated Mar. 1, 2018, 10 pages.
International Searching Authority/US, International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Extended Search Report issued for European Application No. 15800043.0-1115 dated Apr. 16, 2018, 11 pages.

* cited by examiner

DEVICES WITH REDUCED SWEAT VOLUMES BETWEEN SENSORS AND SWEAT GLANDS

CROSS-REFERENCE TO RELATED APPLICATIONS

This application relates to U.S. Provisional Application Nos. 62/003,675, 62/003,715, 62/003,692, all filed May 28, 2014, 62/074,295, filed Nov. 3, 2014, 62/114,835, filed Feb. 11, 2015, and 62/141,327, filed Apr. 1, 2015, the disclosures of which are hereby incorporated by reference herein in their entirety.

BACKGROUND OF THE INVENTION

Sweat sensing technologies have enormous potential for applications ranging from athletics, to neonates, to pharmacological monitoring, to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of medical literature utilizes the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publically perceived capability and opportunity space for sweat sensing.

Of all the other physiological fluids used for bio monitoring (e.g. blood, urine, saliva, tears), sweat has arguably the most variable sampling rate as its collection methods and variable rate of generation both induce large variances in the effective sampling rate. Sweat is also exposed to numerous contamination sources, which can distort the effective sampling rate or concentrations. The variable sampling rate creates a challenge in providing chronological assurance, especially so in continuous monitoring applications.

For example, consider the difficulty of sampling sweat in a sweat sensing patch with a large sweat volume that could mix up sweat previously generated with the newly generated sweat that is intended to be measured to represent a measurement of sweat solutes in real time or near real time. Techniques exist to reduce the sweat volume, such as simply bringing standard sensors closer to skin, but even so the sweat volume is not completely eliminated. Furthermore, space between sweat glands contains the skin surface, which is not a source of sweat, therefore not contributing and of value to sweat sensing. Furthermore, the skin surface can cause contamination of the sweat signal by microbes on skin, by dead skin cell biomarkers, by contaminants on or in skin, or by diffusion of contaminates from the body to the skin surface.

Traditional methods of solving the above problem include those reported frequently in the clinical literature, such as coating the skin with petroleum jelly or oil through which sweat can push. However, these techniques have been demonstrated only for sweat collection and are not inherently compatible with a wearable sensor. For example, petroleum jelly would wet against the sensor and effectively seal it from any sweat. Furthermore, other possible sweat pressure activated techniques that are not made of gels or liquids must somehow be affixed to skin with a strategy that confines the sweat horizontally (such that it does not spread all over the skin surface, else sweat pressure activation is not possible). Conventional approaches will not work with wearable sensors, and inventive steps are required for enablement. Clearly, the state of art is lacking in inventions to properly reduce the volume between sensors and skin. Reducing sweat volume is critical for fast sampling times or sampling times having very low sweat rates, but also may be critical for prolonged stimulation (i.e., where less stimulation is required) and for improving biomarker measurements since, for many biomarkers, a low sweat rate is required to match biomarker concentrations in sweat to that found in blood.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. With such a new invention, sweat sensing could become a compelling new paradigm as a biosensing platform.

SUMMARY OF THE INVENTION

The present invention provides a sweat sensor device capable of reduced volume between the sensors and sweat glands, which decreases the sampling interval. In one embodiment, a sweat sensor device for sensing sweat on the skin includes one or more sweat sensors and a volume-reducing component that provides a volume-reduced pathway for sweat between the one or more sweat sensors and sweat glands in said skin when said device is positioned on said skin. The volume-reducing component may include a volume-reducing material and a pressure-permeated component, a sweat dissolvable material, a mechanically compliant material for conforming to said skin, an adhesive with a vertically anisotropic sweat pathway, microcapsules including a barrier material, and combinations thereof.

In one embodiment, a sweat sensor device includes one or more sweat sensors and a volume-reducing component that provides a volume-reduced pathway for sweat between the one or more sweat sensors and sweat glands in skin when the device is positioned on the skin. The volume-reduced pathway includes a predetermined pathway across said sensors for sweat. One or more sensors has a sampling interval when sensing sweat, and the volume reduced pathway decreases the sampling interval for one or more sensors.

In one embodiment, a sweat sensor device includes one or more sweat sensors and a volume-reducing component that provides a volume-reduced pathway for sweat between the one or more sweat sensors and sweat glands in the skin when the device is positioned on the skin. A coating of sweat-wetting material is on one or more sweat sensors.

In one embodiment, a sweat sensor device includes one or more sweat sensors and a volume-reducing component that provides a volume-reduced pathway for sweat between the one or more sweat sensors and sweat glands when said device is positioned on said skin, where the volume-reducing component includes a plurality of enclosed volumes.

BRIEF DESCRIPTION OF THE DRAWINGS

The objects and advantages of the present invention will be further appreciated in light of the following detailed descriptions and drawings in which.

DEFINITIONS

Figure 1:
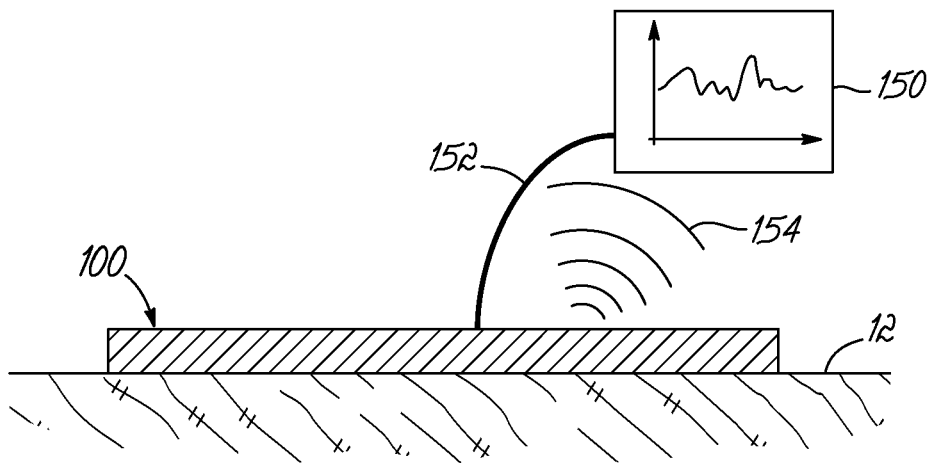
FIG. 1 is a cross-sectional view of at least a portion of a wearable device or patch for sweat biosensing.

As used herein, "continuous monitoring" means the capability of a device to provide at least one measurement of sweat determined by a continuous or multiple collection and sensing of that measurement or to provide a plurality of measurements of sweat over time.

As used herein, "chronological assurance" is an assurance of the sampling rate for measurement(s) of sweat or solutes in sweat in terms of the rate at which measurements can be made of new sweat or its new solutes as originating from the body. Chronological assurance may also include a determination of the effect of sensor function, potential contamination with previously generated sweat, previously generated solutes, other fluid, or other measurement contamination sources for the measurement(s).

As used herein, "determined" may encompass more specific meanings including but not limited to: something that is predetermined before use of a device; something that is determined during use of a device; something that could be a combination of determinations made before and during use of a device.

As used herein, "sweat sampling rate" is the effective rate at which new sweat or sweat solutes, originating from the sweat gland or from skin or tissue, reaches a sensor which measures a property of sweat or its solutes. Sweat sampling rate, in some cases, can be far more complex than just sweat generation rate. Sweat sampling rate directly determines or is a contributing factor in determining the chronological assurance. Times and rates are inversely proportional (rates having at least partial units of 1/seconds), therefore a short or small time required to refill a sweat volume can also be said to have a fast or high sweat sampling rate. The inverse of sweat sampling rate (1/s) could also be interpreted as a "sweat sampling interval" (s). Sweat sampling rates or intervals are not necessarily regular, discrete, periodic, discontinuous, or subject to other limitations. Like chronological assurance, sweat sampling rate may also include a determination of the effect of potential contamination with previously generated sweat, previously generated solutes, other fluid, or other measurement contamination sources for the measurement(s). Sweat sampling rate can also be in whole or in part determined from solute generation, transport, advective transport of fluid, diffusion transport of solutes, or other factors that will impact the rate at which new sweat or sweat solutes reach a sensor and/or are altered by older sweat or solutes or other contamination sources. Sensor response times may also affect sampling rate.

As used herein, "sweat stimulation" is the direct or indirect causing of sweat generation by any external stimulus, the external stimulus being applied for the purpose of stimulating sweat. One example of sweat stimulation is the administration of a sweat stimulant such as pilocarpine. Going for a jog, which stimulates sweat, is only sweat stimulation if the subject jogging is jogging for the purpose of stimulating sweat.

As used herein, "sweat generation rate" is the rate at which sweat is generated by the sweat glands themselves. Sweat generation rate is typically measured by the flow rate from each gland in nL/min/gland. In some cases, the measurement is then multiplied by the number of sweat glands from which the sweat is being sampled.

As used herein, "measured" can imply an exact or precise quantitative measurement and can include broader meanings such as, for example, measuring a relative amount of change of something. Measured can also imply a binary measurement, such as 'yes' or 'no' type measurements.

As used herein, "sweat volume" is the fluidic volume in a space that can be defined multiple ways. Sweat volume may be the volume that exists between a sensor and the point of generation of sweat or a solute moving into or out of sweat from the body or from other sources. Sweat volume can include the volume that can be occupied by sweat between: the sampling site on the skin and a sensor on the skin where the sensor has no intervening layers, materials, or components between it and the skin; or the sampling site on the skin and a sensor on the skin where there are one or more layers, materials, or components between the sensor and the sampling site on the skin.

As used herein, "solute generation rate" is simply the rate at which solutes move from the body or other sources into sweat. "Solute sampling rate" includes the rate at which these solutes reach one or more sensors.

As used herein, "microfluidic components" are channels in polymer, textiles, paper, or other components known in the art of microfluidics for guiding movement of a fluid or at least partial containment of a fluid.

As used herein, "state void of sweat" is where a space or material or surface that can be wetted, filled, or partially filled by sweat is in a state where it is entirely or substantially (e.g. >50%) dry or void of sweat.

As used herein, "advective transport" is a transport mechanism of a substance or conserved property by a fluid due to the fluid's bulk motion.

As used herein, "diffusion" is the net movement of a substance from a region of high concentration to a region of low concentration. This is also referred to as the movement of a substance down a concentration gradient.

As used herein, "convection" is the concerted, collective movement of groups or aggregates of molecules within fluids and rheids, either through advection or through diffusion or a combination of both.

As used herein, a "volume-reduced pathway" is a sweat volume that has been reduced by addition of a material, device, layer, or other body-foreign substance, which therefore increases the sweat sampling interval for a given sweat generation rate. This term can also be used interchangeably in some cases with a "reduced sweat pathway", which is a pathway between eccrine sweat glands and sensors that is reduced in terms of volume or in terms of surfaces wetted by sweat along the pathway. Volume reduced pathways or reduced sweat pathways include those created by sealing the surface of skin, because skin can absorb or exchange water and solutes in sweat which could increase the sweat sampling interval and/or cause contamination, which can also alter the accuracy or duration of the sweat sampling interval.

As used herein, "volume reducing component" means any component which reduces the sweat volume. In some cases, the volume reducing component is more than just a volume reducing material, because a volume reducing material by itself may not allow proper device function (e.g., the volume reducing material would need to be isolated from a sensor for which the volume reducing material could damage or degrade, and therefore the volume reducing component may comprise the volume reducing material and at least one additional material or layer to isolate volume reducing material from said sensors).

As used herein "pressure-permeated component" is a component which requires pressure to be permeated by sweat. Pressure permeated components may also include all known one-way valves which are opened by pressure, including those known by those skilled in the art of microfluidics. Sweat can be occluded using pressure. In one example, antiperspirants use pressure to stop sweat. Therefore, a pressure permeated component can be designed to work at the low pressures that correlate with low sweat rates.

As used herein, a "horizontally-confining component" is a component that does not allow fluid to substantially spread horizontally along the skin surface.

As used herein, a "curable fluid or gel" is a fluid or gel that either dries or chemically cures into a solid.

DETAILED DESCRIPTION OF THE INVENTION

To understand the proper numerical values or representations of sweat sampling rate and therefore chronological assurance, sweat generation rate and sweat volumes should be understood. The number of active sweat glands varies greatly among different people, though comparisons between different areas (ex. axillae versus groin) show the same directional changes (certain areas always have more active sweat glands while others always have fewer). Estimates of the number of glands per $cm^2$ for different areas of the body include: around 370 sweat glands per $cm^2$ for the palm; 200 for the back of the hand; 175 for the forehead; 155 for the breast, abdomen, and forearm; and 60-80 for the back and legs. Assuming use of a sweat gland density of $100/cm^2$, a sensor that is 0.55 cm in radius (1.1 cm in diameter) would cover about 1 $cm^2$ area or approximately 100 sweat glands. Now, consider some sweat generation rates provided from the book: 'Dermatology: an illustrated color text" 5th edition. The human body excretes a minimum of 0.5 liter per day of sweat, and has 2.5 million sweat glands on average and there are 1440 minutes per day. For prepubescent children, these values for total sweat or sweat generation rate are typically lower. For 2.5 million glands that is rate of 0.2 µl per gland per day or 0.14 nl/min/gland. This is the minimum 'average' sweat generation rate, on average, with some possible exceptions being where sweating increases slightly on its own (such as measuring sleep cycles, etc.). Again, from 'Dermatology: an illustrated color text" 5th edition, the maximum sweat generated per person per day is 10 liters which on average is 4 µL per gland maximum per day, or about 3 nL/min/gland. This is about 20× higher than the minimum sweat generation rate.

The maximum stimulated sweat generation rate according to Buono 1992, J. Derm. Sci. 4, 33-37, "Cholinergic sensitivity of the eccrine sweat gland in trained and untrained men", the maximum sweat generation rate by pilocarpine stimulation are about 4 nL/min/gland for untrained men and 8 nL/min/gland for trained (exercising often) men. Other sources indicate maximum sweat generation rates of an adult can be up to 2-4 liters per hour or 10-14 liters per day (10-15 g/min·$m^2$), which based on the per hour number translates to 20 nL/min/gland or 3 nL/min/gland. Sweat stimulation data from "Pharmacologic responsiveness of isolated single eccrine sweat glands" by K. Sato and F. Sato (the data was for extracted and isolated monkey sweat glands, which are very similar to human ones) suggests a sweat generation rate up to about 5 nL/min/gland is possible with stimulation, and several types of sweat stimulating substances are disclosed. For simplicity, we can assume for use in calculations in the present invention (but not so limit the present invention) that the minimum sweat generation rate on average is about 0.1 nL/min/gland and the maximum sweat generation rate is about 5 nL/min/gland, which is about a 50× difference between the two.

Based on the assumption of a sweat gland density of 100/cm$^2$, a sensor that is 0.55 cm in radius (1.1 cm in diameter) would cover about 1 cm$^2$ area or approximately 100 sweat glands. Next, assume a sweat volume under a skin-facing sensor (space between the sensor and the skin) of 50 μm average height or 50×10$^{-4}$ cm, and that same 1 cm$^2$ area, which provides a sweat volume of 50E-4 cm$^3$ or about 50E-4 mL or 5 μL of volume. With the maximum sweat generation rate of 5 nL/min/gland and 100 glands, it would require a 10 minutes to fully refresh the sweat volume (using first principles/simplest calculation only). With the minimum sweat generation rate of 0.1 nL/min/gland and 100 glands, it would require 500 minutes or 8 hours to fully refresh the sweat volume. If the sweat volume could be reduced by 10× to a volume height of 5 μm roughly, the max and min times would be 1 minute and 1 hour, respectively, but the min time would also be subject to diffusion and other contamination issues (and 5 μm dead volume height would be technically challenging). Times and rates are inversely proportional (rates having at least partial units of 1/s), therefore a short time required to refill the sweat volume can also be said to have a fast or high sweat sampling rate.

The space between the sensor and the skin could include a microfluidic component. For example, a 25 μm thick piece of paper or glass fiber covering an area of 1 cm$^2$ would equate to a volume of 2.5 μL; if the paper was 50% porous (50% solids), then the sweat volume would be 1.25 μL. With the maximum sweat generation rate of 5 nL/min/gland and 100 glands, it would require 2.5 minutes to fully refresh the sweat volume. With the minimum sweat generation rate of 0.1 nL/min/gland and 100 glands it would require about 100 minutes to fully refresh the sweat volume. "Fully refresh" is a term that in some cases should be interpreted loosely unless further details or calculations are provided. Because of mixing and diffusion over time, the moment of having a "fresh sweat volume" must be determined using finer details of the specific usage and device and situation in question.

The above examples could in some cases be interpreted to provide a sampling interval for sweat, that is the sampling interval would be roughly how long it would require for sweat to fill, or refill, space, in some cases a space where significant diffusion, mixing, and contamination could occur. A sampling interval for sweat could also be more broadly interpreted to include the actual transport, diffusion, or contamination times of those aspects of sweat that are to be measured. Sampling intervals could vary widely. For example, because small ions may diffuse much more readily than large proteins, both could be measured solutes that are affecting the sampling interval. Sampling intervals could vary widely, for example, based on finer aspects of device design, such as designs where sweat is always flowing forward from skin to sensors and beyond versus devices where, somewhere between the sensors and the skin, there are one or more dead or stagnant volumes of sweat. Therefore, the term sampling interval should be interpreted broadly and in some cases will need to be determined experimentally on a case-by-case basis for each aspect of sweat that is to be measured.

Sweat stimulation, or sweat activation, can be achieved by known methods. For example, sweat stimulation can be achieved by simple thermal stimulation, by orally administering a drug, by intradermal injection of drugs such as methylcholine or pilocarpine, and by dermal introduction of such drugs using iontophoresis. A device for iontophoresis may, for example, provide direct current and use large lead electrodes lined with porous material, where the positive pole is dampened with 2% pilocarpine hydrochloride and the negative one with 0.9% NaCl solution. Sweat can also be controlled or created by asking the subject using the patch to enact or increase activities or conditions which cause them to sweat. These techniques may be referred to as active control of sweat generation rate.

The present invention applies at least to any type of sweat sensor device that measures sweat, sweat generation rate, sweat chronological assurance, its solutes, solutes that transfer into sweat from skin, a property of or things on the surface of skin, or properties or things beneath the skin. The present invention applies to sweat sensing devices which can take on forms including patches, bands, straps, portions of clothing, wearables, or any suitable mechanism that reliably brings sweat stimulating, sweat collecting, and/or sweat sensing technology into intimate proximity with sweat as it is generated. Some embodiments of the present invention utilize adhesives to hold the device near the skin, but devices could also be held by other mechanisms that hold the device secure against the skin, such as a strap or embedding in a helmet.

Certain embodiments of the present invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sweat volume sensor; a sweat generation rate sensor; and a solute generation rate sensor. Certain embodiments of the present invention show sub-components of what would be sweat sensing devices with more sub-components needed for use of the device in various applications, which are obvious (such as a battery), and for purpose of brevity and focus on inventive aspects are not explicitly shown in the diagrams or described in the embodiments of the present invention. As a further example, many embodiments of the present invention could benefit from mechanical or other means known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the spirit of the present invention. The present application has specification that builds upon PCT/US13/35092, the disclosure of which is hereby incorporated herein by reference in its entirety.

With reference to FIG. 1, a sweat sensor device 100 is placed on or near skin 12. In an alternate embodiment, the sweat sensor device may be simply fluidically connected to skin or regions near skin through microfluidics or other suitable techniques. Device 100 is in wired communication 152 or wireless communication 154 with a reader device 150. In one embodiment of the present invention, reader device 150 would be a smart phone or portable electronic device. In alternate embodiments, device 100 and reader device 150 can be combined. In further alternate embodiments, communication 152 or 154 is not constant and could be a simple one time data download from device 100 once it has completed its measurements of sweat.

Figure 2:
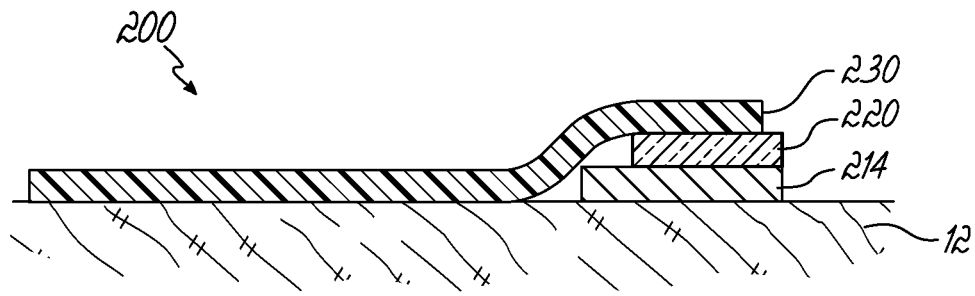
FIG. 2 is a cross-sectional view of at least a portion of a wearable device or patch for sweat biosensing.

With reference to FIG. 2, microfluidic component 230 carries sweat from skin 12 to sensor 220 that is placed on impermeable substrate 214. For example, sensor 220 can be an impedance sensor for a cytokine biomarker, and impermeable substrate 214 can be a polyimide film. Sensor 220 measures one or more solutes in sweat or the presence or flow rate of sweat. Microfluidic component 230 could be, for example, paper, a polymer microchannel, a tube, or a gel, or other means to transport sweat from skin 12 to sensor 220. If the volume of microfluidic component 230 is small, then the sweat flow rate will be higher across the sensor 220 and will mitigate diffusion of contaminating solutes or mixing of fluids collected at previous times. A better chronological assurance is provided by reducing back diffusion of solutes from previously generated sweat that has wicked beyond sensor 220. For continuous monitoring, microfluidic component 230 could wick sweat past the sensor 220 to a hydrogel that continuously absorbs, which therefore pumps sweat from skin 12 and across sensor 220 at the rate at which sweat is provided from the skin.

For an example of device 200 in use, the device could be used with a runner during a race with the runner having a sweat generation rate of 5 nL/min/gland during the race. The microfluidic component could be a 25 µm thick piece of paper or glass fiber covering 100 glands, or 1 cm², equating to a sweat volume of 2.5 µL ($25 \times 10^{-4}$ cm×1 cm×1 cm=$25 \times 10^{-4}$ cm³=$2.5 \times 10^{-3}$ mL). If the paper were 50% porous (50% solids), then the sweat volume would be 1.25 µL. Therefore, the sweat sampling rate, for example, could be calculated as 1.25 µL/(5 nL/min/gland×100 glands)=2.5 min. Therefore, sweat sensing device 200 could provide a chronological assurance of 2.5 minutes, meaning that the data the device reports could be interpreted to represent at least one physiological measurement of the runner that is determined from newly generated sweat within a window of time of approximately 2.5 minutes. This is a first order type calculation, which in some cases could be highly accurate for looking at, for example, the onset of a significant increase of a particular solute in sweat. Note that this calculation neglects sweat volume increases due to factors such as roughness of skin.

Figure 3:
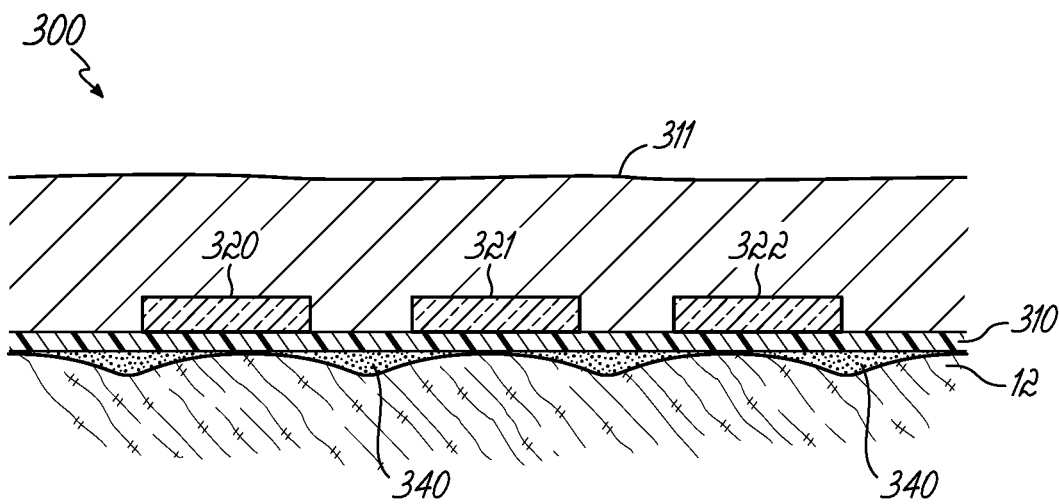
FIG. 3 is a cross-sectional view of at least a portion of a wearable device or patch for sweat biosensing.

With reference to FIG. 3, device 300 includes material 311 that carries two or more sensors, 320, 321 and reference electrode 322, and has below it adhesive 310. Volume 340 is between adhesive 310 and skin 12. Adhesives can be pressure sensitive, liquid, tacky hydrogels, which promote robust electrical, fluidic, and iontophoretic contact with skin. Material 311 could be, for example, porous to sweat, wick sweat like a hydrogel or textile, or be impermeable to sweat. Skin 12 has a roughness to it, which is illustrated in FIG. 3. Even with adhesive 310, in some embodiments of the present invention, volume 340 would exist, which in combination with the available porous volume or sweat uptake volume of adhesive 310 could provide a sweat volume between skin 12 and sensors 320, 321 and electrode 322. Sensor 320 could be an ion-selective electrode to measure sodium, sensor 321 could be an electrical impedance spectroscopy sensor to measure cortisol, and sensor 322 could be a drift-free Ag/AgCl reference electrode. Sweat generation rate could be measured by sodium concentration by sensor 320, and sweat generation rate could also be measured by impedance by sensor 321, providing together a measured sweat generation rate. Reference electrode 322 should preferably be centimeters or more away from sensor 321 if the most accurate impedance measurement into the skin is to be measured.

For an example of device 300 in use, device 300 could be adhered to a skin location that has a depth of grooves of 50 µm (averaged height of volume 340 could be 25 µm). If sensor 320 had an area of 10 mm², and the volume of adhesive 310 was negligible, the predetermined sweat volume would be at least 250 nL. From a calibrated look-up table for sweat pore density based on placement location on the body, an average of 10 pores under the sensor 320 would be determined. If the sweat generation rate was 1 nL/min/gland, the effective sweat flow rate would be 10 nL/min, and the sweat sampling interval would therefore be 25 minutes. If the sweat rate were lower, for example, 0.1 nL/min/gland, the sampling interval would be on the order of hours. Because this is a relatively slow sampling interval for some applications, effects of diffusion and other contamination may need to be incorporated for some types of measurements. Skin wrinkles can be tens of microns in depth, with a roughness that can be greater than 10 µm. The skin or device can deform, swell, or change in physical geometry. Some skin, as it becomes moist, swells and reduces sweat flow rate (especially finger tips and feet where skin is thick). If the sweat volume could be reduced, a faster sweat sampling rate could be achieved, for example, if the grooves of skin could be filled with a filler material of some sort, the sweat sampling rate could be doubled or even more.

Figure 4A:
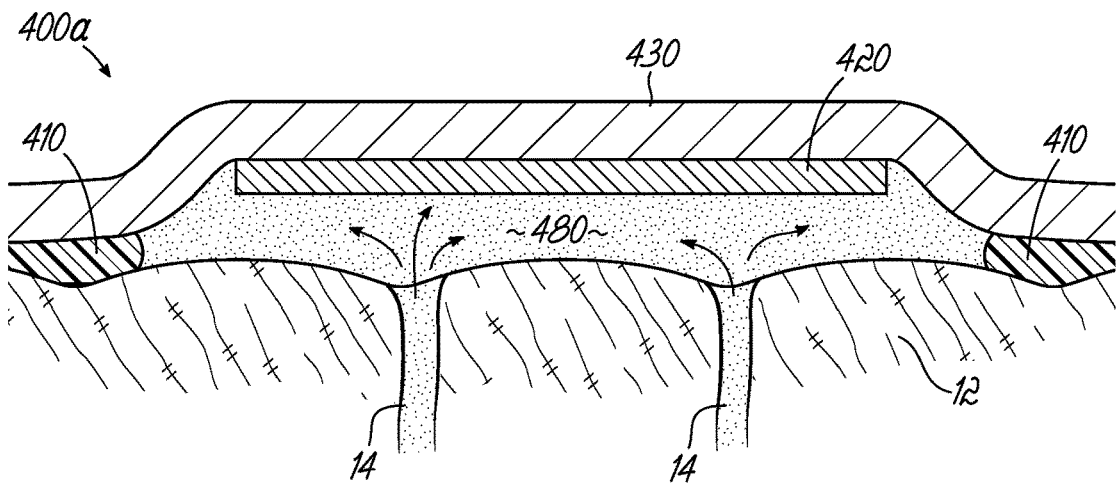
FIG. 4A is a cross-sectional view of at least a portion of a conventional wearable device or patch for sweat biosensing.

With reference to FIG. 4A, device 400a includes material 430, which is a sweat absorbing material such as textile or gel. The device 400a includes at least one sensor 420 and an adhesive 410. The locations of sweat ducts 14 are also noted. The sweat volume 480 between the sensor 420 and ducts 14 is also noted diagrammatically and represents the effective volume or flow path for new sweat as it leaves the ducts and reaches the sensor 420. In the illustrated embodiment, the device 400a has no sweat volume reducing component. Using a first principles calculation, the sampling volume can be calculated accordingly as the volume divided by the incoming flow rate of new sweat. Those of ordinary skill in the art will recognize that more detailed calculations may be made. For example, assume 140 glands/cm² (e.g., the abdomen), a 2.5 mm diameter sensor, a sensor gap from skin of 15 µm and an effective gap due to the roughness of skin of 15 µm as well (30 µm total effective gap). The filling time or sampling interval for this volume would be 40 min and 4 min for 0.5 and 5 nL/min/gland, respectively. Again, the actual sampling interval will be slower in practice due to non-uniform sweat flow rates between the sensor 420 and the skin 12 and due to factors such as diffusion of solutes and sensor response time. This further emphasizes the need to reduce the sweat volume 480. Exact calculations or predictions of sampling interval and sweat volume are not required to reduce sweat volume 480. Rather, embodiments of the present invention illustrate a reduced sweat volume and decreased sampling interval, regardless of the level of detail considered for understanding the sampling interval.

Figure 4B:
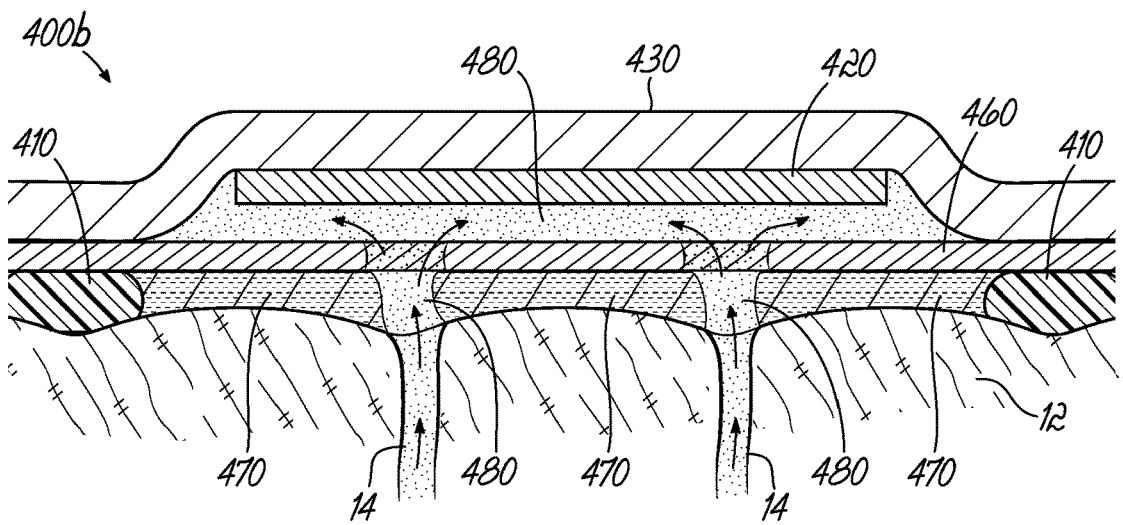
FIGS. 4B-4D are cross-sectional views of at least a portion of devices according to various embodiments of the present invention.

With reference to FIG. 4B, device 400b includes features of FIG. 4A and further includes a volume reducing component. In the illustrated embodiment, the volume reducing component includes a pressure-permeated component 460 and a volume reducing material 470. The device 400b also includes a sweat absorbing material 430 and an adhesive 410, which is co-planar with the volume reducing material 470. The device 400b includes a sweat stimulation source and driving electrode (not shown) for sudo-motor axon reflex sweat stimulation of sweat that can reach sensor 420. The volume reducing component reduces the sweat volume 480 compared to a case where the volume reducing component would not be used (e.g., sweat volume 480 in FIG.

4A). In this embodiment, the volume reducing component is more than just a volume reducing material because a volume reducing material by itself may not allow proper device function. For example, the volume reducing material 470 could be petroleum jelly, which if used alone in device 400b could coat the surface of the sensor 420 and render it inoperable. The volume reducing material 470 may preferably be immiscible with sweat and various sweat solutes. Therefore, by further example, the pressure-permeated component 460 may be a microporous membrane with pores small enough such that viscous gel, such as petroleum jelly, would not permeate it at all or would not permeate it quickly, whereas a much lower viscosity fluid, such as sweat, would much more rapidly permeate through the pressure-permeated component 460. Because the pressure permeated component 460 is pressure-permeated, sweat will only or will preferentially permeate the component 460 near the sweat ducts 14 themselves. As a result of reducing the available sweat volume, the device 400b could have a faster sweat sampling rate. The embodiment shown in FIG. 4B is capable of reducing the sweat volume 480 by 2× or more compared to the embodiment of FIG. 4A. Sweat volume 480 may also represent a "volume-reduced pathway." The portion of the volume-reduced pathway between skin 12 and the pressure-permeated component 460 is formed in the illustrated embodiment by the pressure of sweat generation itself. In this regard, the hydraulic pressure of the sweat coming from the sweat ducts 14 must be able to adequately displace at least a portion the volume reducing material 470 in order to form part of the volume-reduced pathway 480 within the volume reducing material 470. In one embodiment, the volume reducing material 470 is petroleum jelly or a similar material (i.e. not a solid) such that the sweat may generate a pathway through the material 470. Instead, or in addition, the volume reducing material 470 in one embodiment may include a network of hydrophilic wicking fibers or pores (not shown) that form the portion of the sweat volume 480 within the volume reducing material 470.

Figure 4C:
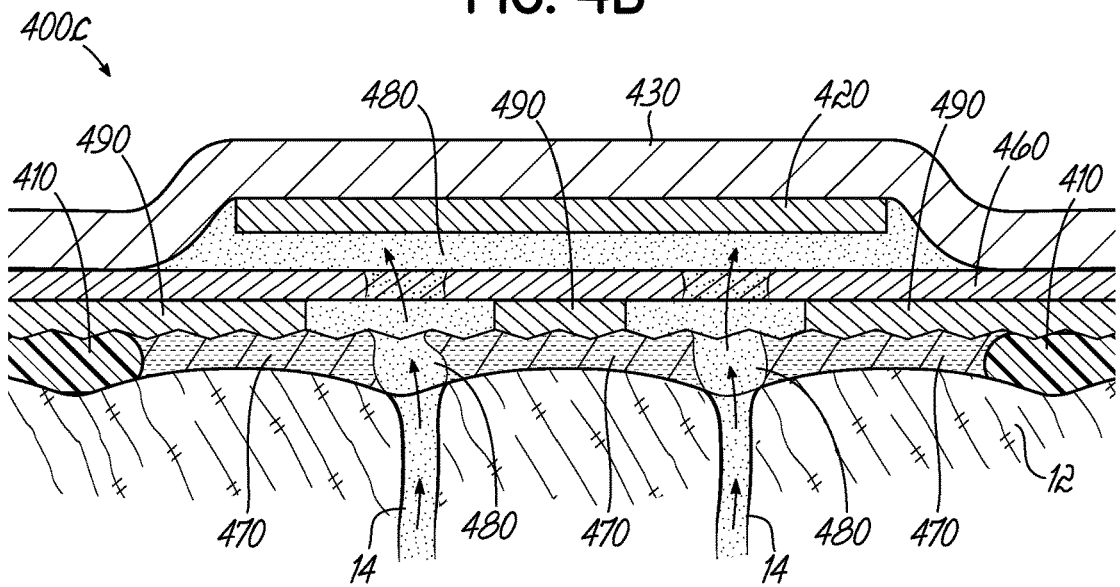

With reference to FIG. 4C, device 400c includes features of FIGS. 4A and 4B, an optional spacer material 410, and further includes a sweat dissolvable material 490. The volume reducing material 470 could be a material with high viscosity, gel-like behavior, or other properties that make it difficult to use in concert with the pressure-permeated component 460. By way of example, the volume reducing material 470 could clog the pores in the pressure-permeated component 460 and the pressure of sweat generation may then be inadequate for allowing sweat to push through the pressure-permeated component 460. Such difficulty can be resolved by the addition of the dissolvable material 490. By way of example, the sweat dissolvable material 490 could be constructed of materials such as sucrose, table salt, polyvinyl alcohol, polyethylene oxide, or any other suitable material. The presence of sweat dissolvable material 490 enhances the reduction in sweat volume and resultant decrease in sampling interval provided by the volume reducing component.

Embodiments of the present invention may include features, surfactants, or other aspects that promote wetting of sweat to dissolvable material 490 or wetting of sweat through volume reducing material 470 to pressure-permeated component 460. All such techniques are herein referred to as sweat-wetting promoting features. In the embodiment illustrated in FIG. 4C, dissolvable material 490 may be a microreplicated film with spikes to promote wetting and dissolution by sweat. Without a non-planar rough or spiky surface, even with sweat pressure, a sweat impermeable film of volume reducing material 470 may exist longer than desired between sweat and the dissolvable material 490. However, embodiments of the present invention may include a dissolvable material 490 having a non-spiky surface. In an exemplary embodiment, dissolvable material 490 could be a coating or film on pressure-permeated component 460. In an embodiment where pressure-permeated component 460 is a membrane with pores, dissolvable material 490 could be a material at least partially plugging the pores of pressure-permeated component 460. In one aspect of the present invention, embodiments may include features that increase the dissolution rate of sweat through sweat dissolvable material 490 through, for example, improved sweat permeation into dissolvable material 490 and/or by reducing the dissolvable mass. In one embodiment, the dissolvable material 490 could be a microporous polymer containing pores or voids. In this regard, the microporous nature of the dissolvable material 490 increases the sweat permeability and, thus, the dissolution rate.

Figure 4D:
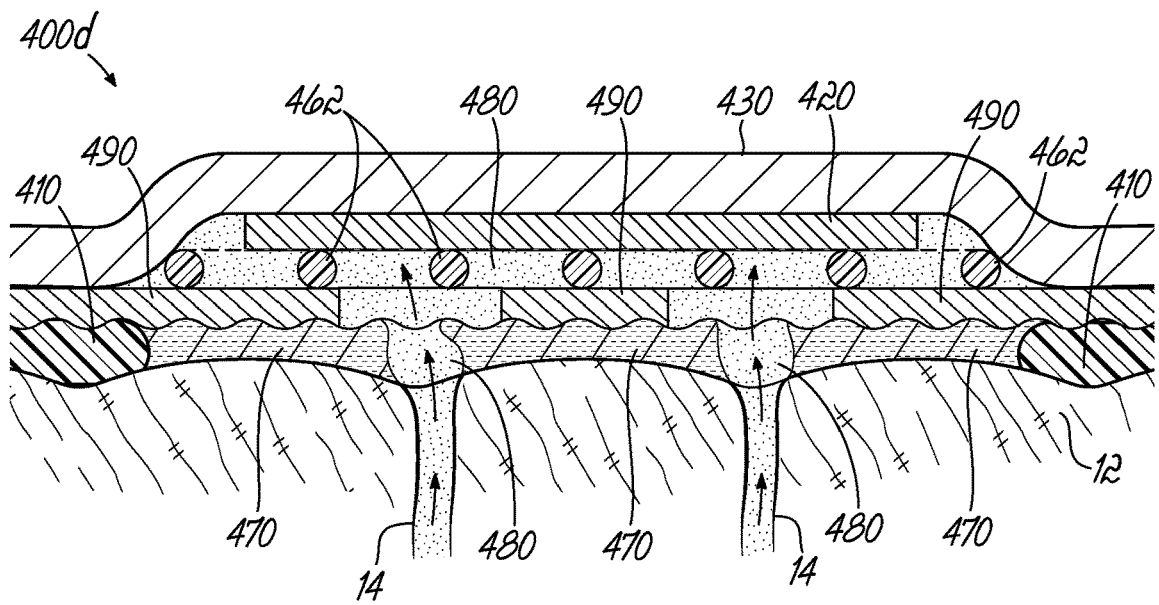

In an alternate embodiment, sweat dissolvable material 490 could include a non-sweat dissolvable plastic support that would maintain the physical integrity of sweat dissolvable material 490. FIG. 4D illustrates a device 400d where sweat dissolvable material 490 includes a non-dissolvable plastic mesh 462. Device 400d is shown after the sweat has dissolved a portion of the sweat dissolvable material 490 and the sweat volume 480 is established while the device 400d is measuring sweat. Those of ordinary skill will recognize that other configurations of sweat dissolvable material 490 are possible to enhance the reduction in sweat sampling intervals and reduction in sweat volumes provided by the volume reducing component.

Figure 4E:
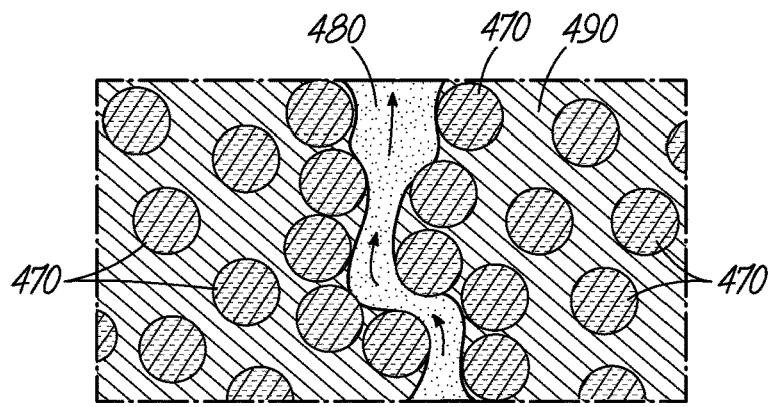
FIGS. 4E and 4F are cross-sectional views of at least a portion of devices according to various embodiments of the present invention showing alternate configurations.
Figure 4F:
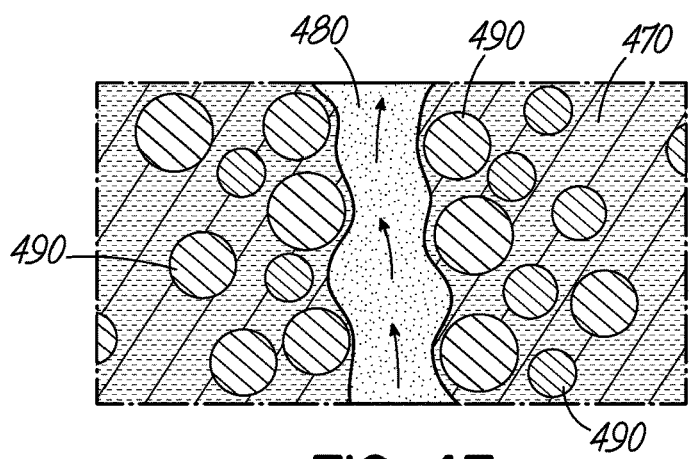

With reference to FIGS. 4E and 4F, only a portion of sweat sensing devices according to various embodiments of the present invention are shown. FIGS. 4E and 4F illustrate embodiments where dissolvable materials 490 and volume reducing materials 470 are used in alternate arrangements where sweat is able to form a path based on pressure and/or the dissolving of dissolvable material 490 such that a reduced sweat volume 480 is provided. Those of ordinary skill in the art will recognize that other alternate arrangements may be possible.

Figure 5:
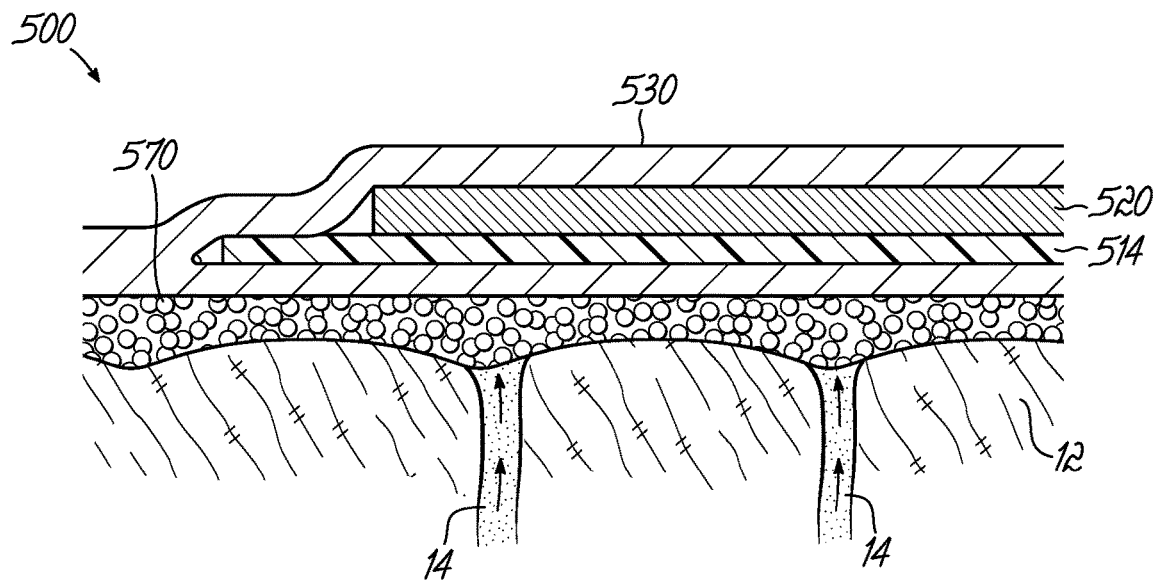
FIG. 5 is a cross-sectional view of at least a portion of a device according to one embodiment of the present invention including beads.

With reference to FIG. 5, device 500 includes a microfluidic component 530, a sensor 520, and an impermeable substrate 514 carrying said sensor 520. The grooves in skin 12 are filled with beads 570. "Beads" conventionally refers to spherical particles; however, the meaning of "beads" within the present invention includes any particle type that allows the particles to move over each other and to pack together. The beads 570 may be hydrophilic such that they are readily wetted by sweat fluid. The beads 570 could be adhered to the microfluidic component 530 prior to patch application and, as patch 530 is applied, they move into grooves in skin as pressure is applied to the skin 12. The 570 beads could also help fill space above grooves as well. The adhesion of beads 570 to the microfluidic component 530 could be provided by a viscous non-volatile fluid which holds them together, or a solid that dissolves in sweat such as sucrose. For beads 570 that are equal spheres, the densest packing uses approximately 74% of the volume. Random packing of equal spheres generally results in a density of around 64%. The packing, of course, could have a lower density. However, it can be expected that spheres could reduce the sweat volume by 30%, 50%, even up to around 60%. The beads could also be inside an adhesive, the adhesive and beads flowing or conforming enough to provide a volume-reduced pathway for sweat.

Figure 6A:
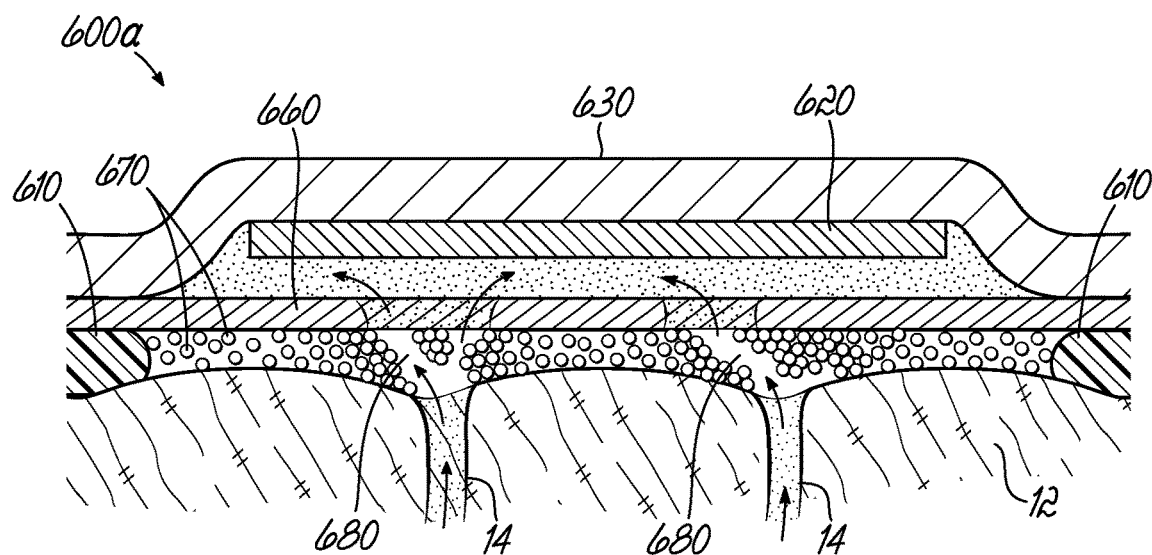
FIG. 6A is a cross-sectional view of at least a portion of a device according to one embodiment of the present invention including one layer of beads.

With reference to FIG. 6A, device 600a includes an absorbing material 630 to wick sweat, at least one sensor 620, an optional membrane or mesh 660, hydrophobic beads 670, and an adhesive 610. The volume reduced pathway 680 is restricted by the hydrophobic beads 670, which may form at least a part of a volume reducing component. By way of example, the beads 670 could be made of any hydrophobic polymer or could be made of non-hydrophobic polymers with a thin coating that renders the beads 670 hydrophobic. In one embodiment, the beads 670 could be made of hydrophobic Teflon. If the beads 670 are coated with a transferable coating, such as a hydrophobic oil or gel, the optional membrane 660 protects sensor 620 from the coating. In this regard, the openings or pores in the membrane or mesh 660 would be smaller than the beads 670. In an embodiment where the beads 670 do not include a transferable coating and the sensor 620 is hydrophilic or coated with hydrophilic material (not shown) to be adequately wetted by sweat, the membrane 660 may be excluded. The membrane 660 could be, for example, a material that is preferentially wetted by sweat as compared to oil and therefore is preferably permeable to sweat. The membrane 660 and beads 670 together may function as a pressure-permeated component. Oil could also come from the surface of skin 12.

Skin oil generation over time can also be problematic. In one aspect of the present invention, the beads 670 may be oleoscopic such that they absorb oil. Including oleoscopic beads 670 may mitigate the effects of skin oil on the functioning of device 600a. By way of example, the beads 670 could be constructed of materials such as those used commercially in Imbiber Beads sold by Imbibitive Technologies. Beads 670 can be any suitable geometry found in numerous types of solid powders or solid particles. As oil absorbing beads absorb oil, they may swell. If, as they swell, the beads become soft and can pack tighter (like Imbiber Beads), the sweat volume will decrease. Additionally, or alternatively, the hydrophobicity of the beads 670 could also allow them to absorb skin oils in spaces between the beads (i.e., be oleophilic in nature).

Figure 6B:
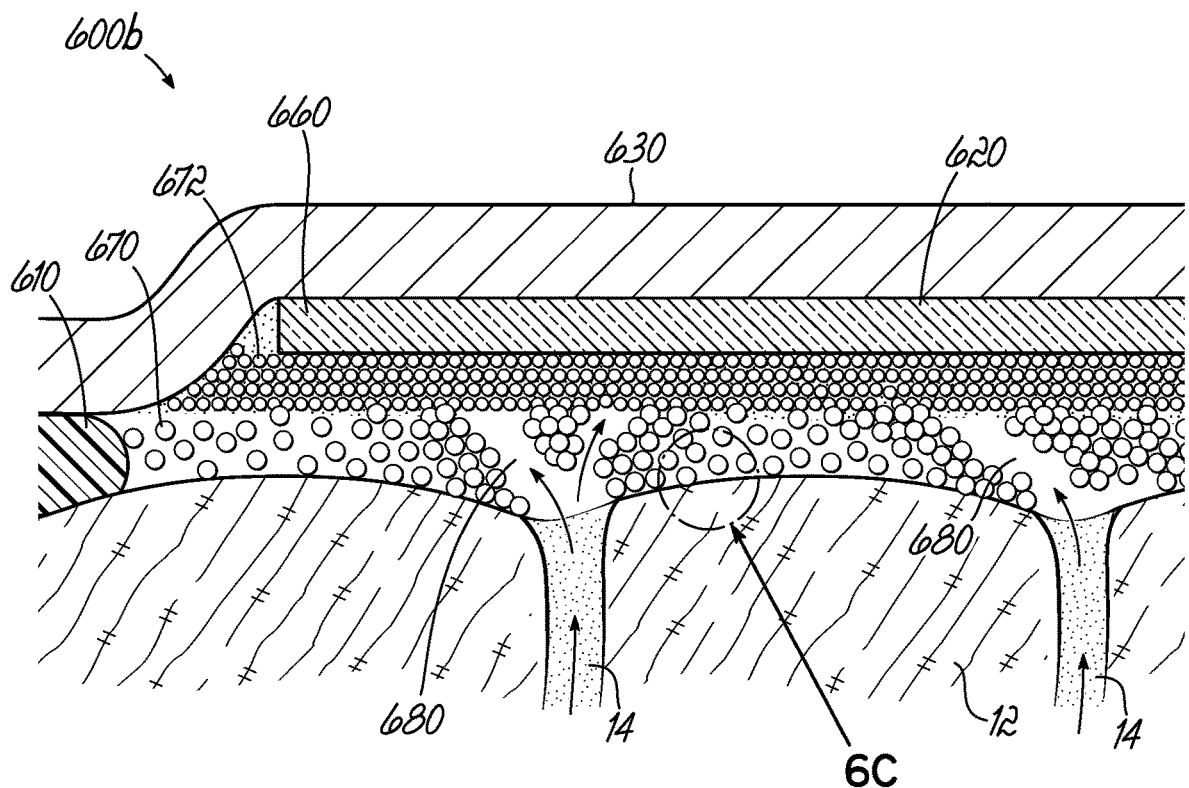
FIG. 6B is a cross-sectional view of at least a portion of a device according to one embodiment of the present invention including two layers of beads.

With reference to FIG. 6B, a device 600b includes features similar to those of device 600a and further includes beads 672 adjacent to hydrophobic beads 670. Beads 672 may be hydrophilic or less hydrophobic than beads 670. Beads 672 could also have the same hydrophobicity but be larger in spacing such that they exhibit a lower Laplace pressure for sweat such that they are preferentially permeated with sweat over the beads 670. The volume reduced pathway 680 is restricted by the hydrophobic beads 670, and a fluidic connection to the sensor 620 is provided by the beads 672. In one embodiment, the beads 672 are rigidly bound such that they stay in place to protect sensor 620 from a transferable coating that might be on the beads 670, similar to the optional membrane or mesh 660 shown in FIG. 6A. Alternatively, in one embodiment, beads 670 are more loosely bound by wax, grease, or other material such that beads 670 can conform to skin 12. The device 600b may be small in area and secured by adhesives around its perimeter or clamped to the skin with a bracelet, strap, or other method. By way of example, the area of device 600b may be between about 0.3 mm$^2$ and about 3 mm$^2$.

In one aspect of the present invention, hydrophobic beads 670 could be coated with a hydrophobic liquid, gel, grease, or powder that is transferable to the surface of skin that would form a hydrophobic coating on skin, skin barrier, or sealant. By way of example, this transferable hydrophobic coating could be a Teflon hydrophobic powder, a viscous hydrophobic silicone fluid, petroleum jelly, or silicone gel.

Figure 6C:
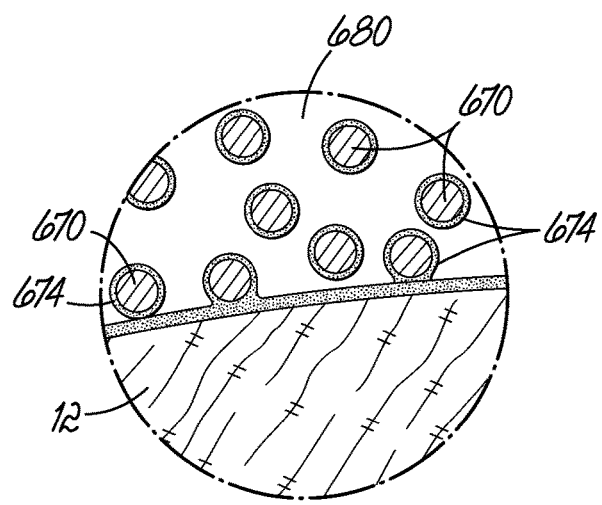
FIG. 6C is an enlarged view of the encircled portion 6C of the device of FIG. 6B.

With reference to FIG. 6C, as the device 600b is applied to the skin, the transferable hydrophobic coating 674 may render the skin hydrophobobic, such that the skin is sealed or impermeable to sweat transport or solute transport in or out of the skin. In one embodiment, the beads 670 in close proximity to the skin 12 may have the transferable coating 674, while the beads 672 in closer proximity to the sensor 620 may not have the coating 674, which would reduce the chance for the coating 674 to reach and interfere with operation of sensor 620.

In embodiments of the present invention where a device or patch includes beads having a coating transferable to the skin, an apparatus may be included for applying the device or patch to the skin that applies pressure to press the device against skin and that provides a longitudinal stress or force to ensure the coating is transferred to the skin. In one embodiment, the beads 670 may be rigidly bonded together until the device is applied to skin 12 to make the application easier. For example, the beads 670 may be bound with a material that, when a stimulus is applied as the device is placed on the skin, allows the beads 670 to flow. The material may, for example, be a wax, other type of hydrophobic coating, or non-hydrophobic adhesive. The stimulus may be, for example, heat. Such a method of applying the device to the skin improves adhesion of the device to the skin.

In one aspect of the present invention, and with further reference to FIGS. 5, 6A, and 6B, the beads 570, 670, 672 could be bound by magnetic forces, which allows them to flow or move under mechanical pressure but holds them together on the patch. In one embodiment, beads 570, 670, 672 are magnetic. Numerous forms of biocompatible magnetic microbeads, polymer or inorganic, are known by those skilled in the art. In another embodiment, beads 570, 670, 672 could also metallic or magentizeable with an external magnetic field (e.g., magnetic permability greater than 1, like some metals), such that they are held in place until beads 570, 670, 672 are applied with the device to skin. For example, the applicator could include a permanent or electronic magnet. As another example, the device may be packaged with a magnetizing component needed to hold the beads in place until after the device is firmly applied to skin.

Particular advantages of the embodiment illustrated in FIG. 6B include the following: (1) a volume reducing material that self-aligns with sweat pores; (2) a volume reducing material which will not damage the sensor operation; and (3) a volume reducing material that conforms to the skin and other aspects of the skin surface (e.g., roughness, wrinkles, hairs, dust fibers, etc.) but which is incompressible, such that external or internal induced mechanical pressures do not damage or alter the volume reduced pathway. Regarding the third advantage, in other words, the volume reducing material may be a mechanically compliant component (i.e., the beads) that is porous to sweat. One of ordinary skill in the art would recognize that alternate materials or configurations that result in such advantages are contemplated by the present invention. An additional advantageous aspect of the present invention discussed above includes applying a hydrophobic seal or barrier coating on the skin during application of the device. In one embodiment, a device could utilize a porous memory foam coated with oil or other type of sealant on its side facing the skin.

As previously discussed, embodiments of the present invention may include a "volume-reduced pathway" for sweat in terms of reducing the pathway away from skin where additional contaminants could enter the skin and alter or confound sweat sensing. Essentially, skin itself is permeable and constitutes an additional space that sweat and sweat solutes can move into or out of as well, therefore in some cases adding to the total effective sweat volume. This is especially true at low sweat generation and/or flow rates, where diffusion of solutes in sweat or in skin becomes comparable in nature to advective transport of solutes in sweat. Therefore, volume-reduced pathway should be interpreted to include such features and aspects discussed below that will hinder or block sweat or solute transport into and out of skin, such that the volume reduced pathway is limited primary to being only above the skin. For example, the embodiment shown in FIG. 6C reduces the transport of sweat or its solutes into and out of skin, and therefore creates a volume reduced pathway that, even at low sweat flow rates, is limited to the space above skin.

Figure 7:
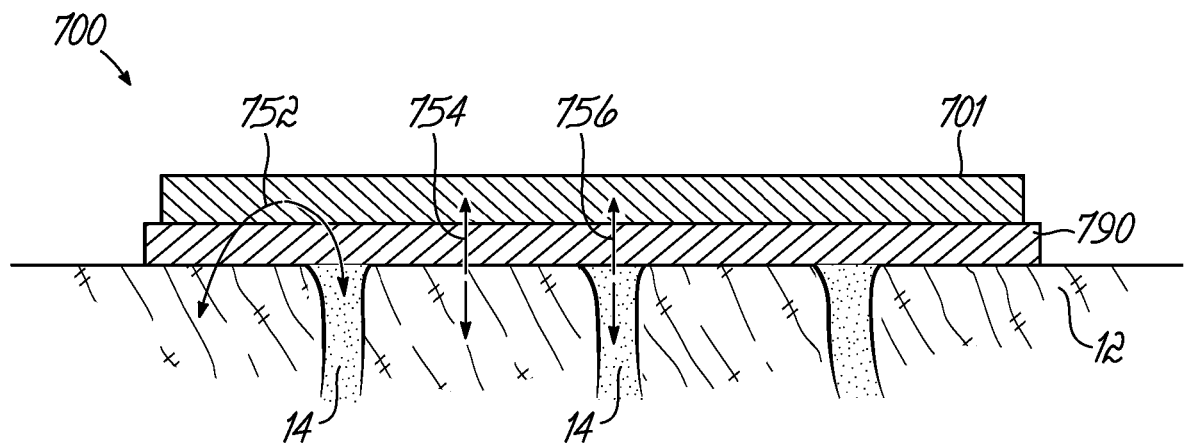
FIG. 7 is a cross-sectional view of a conventional wearable sweat sensing device or patch showing various solute pathways.

With reference to FIG. 7, the conventional transport of solutes from skin 12 to a sensor 701 is shown. For purposes of convenience, sensor 701 is schematically represented as a single element, although sensors may comprise various elements. Element 790 schematically represents the contact between skin 12 and the sensor 701. Those of ordinary skill in the art will recognize that the exact construction or description of element 790 may vary. In one embodiment, element 790 could represent direct contact between the skin 12 and the sensor 701. In another embodiment, element 790 could represent a hydrogel. Solutes in skin or sweat freely or at least partially diffuse through element 790 by pathways 752, 754, and 756. Regarding pathway 754, the skin 12 can absorb water or sweat solutes and can leach out solutes that contaminate sweat, etc. Due to the various transport pathways, sensors will see a partially or substantially mixed signal between solutes coming from sweat ducts 14 and the surface of the skin 12. These signals can in some cases confound a meaningful measurement of one or more solutes in sweat.

Figure 8:
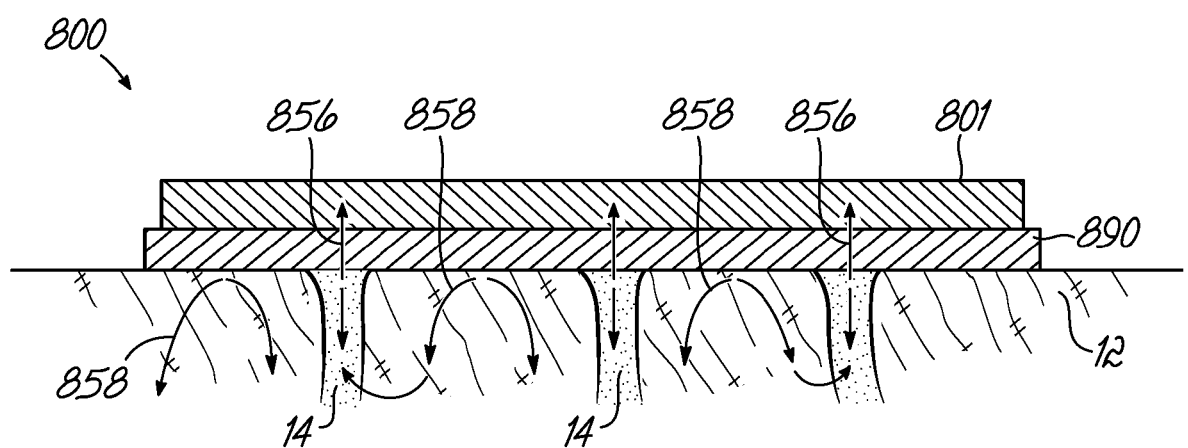
FIG. 8 is a cross-sectional view of at least a portion of a device according to one embodiment of the present invention.

With reference to FIG. 8, an embodiment of the present invention includes a sensor 801 adjacent to an element 890 that is configured to favor transport 856 of solutes in or out of sweat glands or ducts over transport 858 of solutes from in or out of skin or contaminants on the surface of skin. In this regard, "volume reduced pathway" and "sweat volume" include reducing the volume of sweat originating from the skin 12 as opposed to the sweat originating from the ducts 14. Transport can be effected by pressure driven flow, osmosis, electro-osmosis, diffusion, electrophoresis, or other forces suitable to transport solutes in a fluid such as water. One of ordinary skill in the art will recognize that the improvements of transport paths will vary for different solutes and different applications. Element 890 may include features or components discussed in other illustrative embodiments.

Figure 9:
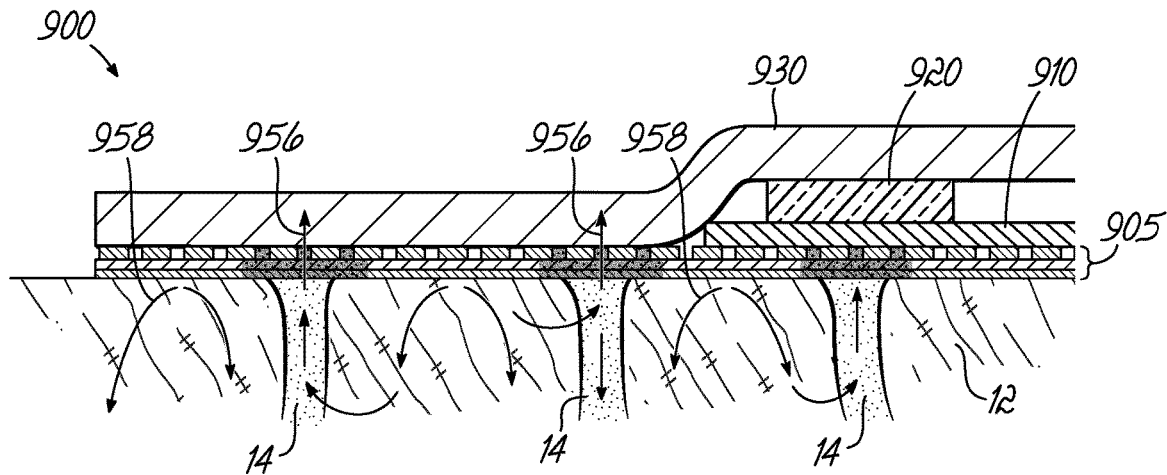
FIG. 9 is a cross-sectional view of at least a portion of a device according to one embodiment of the present invention.

With reference to FIG. 9, an element 905 favors transport 956 of sweat or solutes in sweat and disfavors transport 958 of solutes in or on skin 12, which is discussed in more detail below. Transport 956 of solutes enters a microfluidic component 930 which then allows transport to sensor 920 for detection of solutes. In one embodiment, element 910 is a substrate for supporting sensor 920.

Figure 9A:
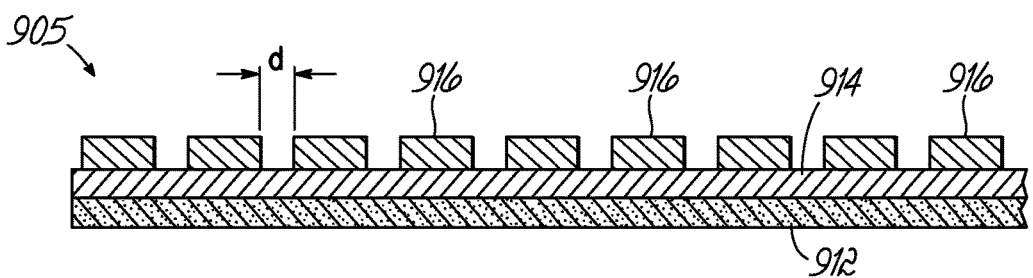
FIG. 9A is an enlarged view of a portion of the device of FIG. 9.

With reference to FIG. 9A, a portion of an element 905 is shown that includes an adhesive 912 able to seal element 905 substantially against the skin 12 such that significant horizontal sweat or solute transport is prevented between adhesive 912 and skin 12. Because skin is non-planar, adhesive 912 is soft or flowing and may partially or fully penetrate the grooves on the surface of skin. Adhesive 912 can be a gel or paste-like material that is pressure permeated. Adhesive or film 914 may be firmer than adhesive 912. Adhesive or film 914 may be provided such that the soft or flowing adhesive 912 does not overly penetrate pores in the membrane or mesh 916. Those skilled in the art will recognize that alternate arrangements and components of element 905 are possible.

In embodiments of the present invention, pressure-permeated components can be a track-etched membrane. By way of example, the track-etched membrane could be one available from Whatman Company or SPI Scientific. In one exemplary embodiment, membrane 916 of FIG. 9A is a track-etched membrane. The pores in the track-etched membrane would act as pressure valves, meaning that a certain pressure of sweat is needed to enable fluid contact through the membrane 916 and into adjacent layers such as, for instance, the microfluidic component 930 shown in FIG. 9. Fluidic contact to the skin would be enabled where sweat glands and ducts exist.

An exemplary calculation follows. Sweat ducts can generate up to 500 mm Hg of pressure, or about 65 kN/m². The Laplace pressure that can be retained by one pore in the membrane 916, with a diameter d (as indicated in FIG. 9A) can be calculated as follows:

$$\Delta p = \frac{2\gamma}{R} \quad R = d/2\cos\theta$$

where p is pressure, gamma is surface tension, R is radius of the pore, d the diameter of the pore, and theta is the fluid contact angle with the side of the pore.

The diameter of a pore needed to withstand the pressure of sweating for the case of 120 degree contact angle and surface tension similar to water may be back-calculated as follows:

$$d = 2R\cos\theta = 4\cos\theta\frac{\gamma}{\Delta p} = 4\cos(120°) * \frac{0.07 \frac{N}{m}}{65,000 \ N/m^2}$$

The result is d=2.15 μm, meaning that the pores would need a diameter greater than that to enable sweat gland pressure to gate fluid connection through membrane 916, but still small enough that other areas of the membrane 916 if wetted by fluid above or below would not, or to a lesser degree, be wetted through by fluid because locally such pressure would be lacking to activate fluid connection through membrane 916. Assuming fluid pinning at the edges of the pore and up to the effect of 180 degrees contact angle, and/or lower sweat pressures, the pore size could be even larger.

In one embodiment of the present invention, adhesives could be hydrogel based and partially permeable to sweat and/or its solutes. In another embodiment, adhesives could be soluble in sweat and cured by ion or pH alteration of adhesive by virtue of applied electrical potential. Many types of silicone adhesives, for example, are pH curable and also water soluble when uncured. The curing could be limited to contact areas of skin, because pH or ions can be limited to alteration only where electrical contact with skin is enabled. In an aspect of the present invention, creating pH gradients on skin, such as with skin iontophoresis, could be used to locally cure an adhesive only where it is in contact with skin (i.e., not above sweat ducts). When sweat is generated, the sweat would dissolve any uncured adhesive and promote free transport of sweat to membrane 916.

The present invention contemplates a variety of configurations of adhesives that create a state of favorable transport for solutes adjacent or above sweat ducts over transport in skin areas outside or substantially outside of sweat ducts. In one embodiment, an adhesive layer may be patterned in a closed-cell lattice pattern, such as a honey comb (hexagonal), that creates closed perimeter seals with the skin hindering horizontal transport of sweat across the skin surface but permitting transport of sweat from sweat ducts to membrane 916. In other words, the adhesives include a plurality of horizontally enclosed volumes, which are further discussed below. Another embodiment of the present invention may include an adhesive in a continuous film that is adequately impermeable to sweat or biomarker transport but that would selectively rupture above sweat ducts due to sweat pressure thus locally enabling biomarker transport through it. In this regard, the adhesive may include a rupturable element capable of being ruptured. The rupturable element could be a thin and fragile solid film that is non-adhesive, which therefore also acts as a pressure-permeated component. Furthermore, external (to the body) positive or negative pressures could be applied to enable or enhance activation of sweat or biomarker transport only above sweat ducts. Those of ordinary skill in the art will recognize that other materials or configurations may create a state of favorable transport for solutes adjacent or above sweat ducts over transport in skin areas outside or substantially outside of sweat ducts.

Figure 10:
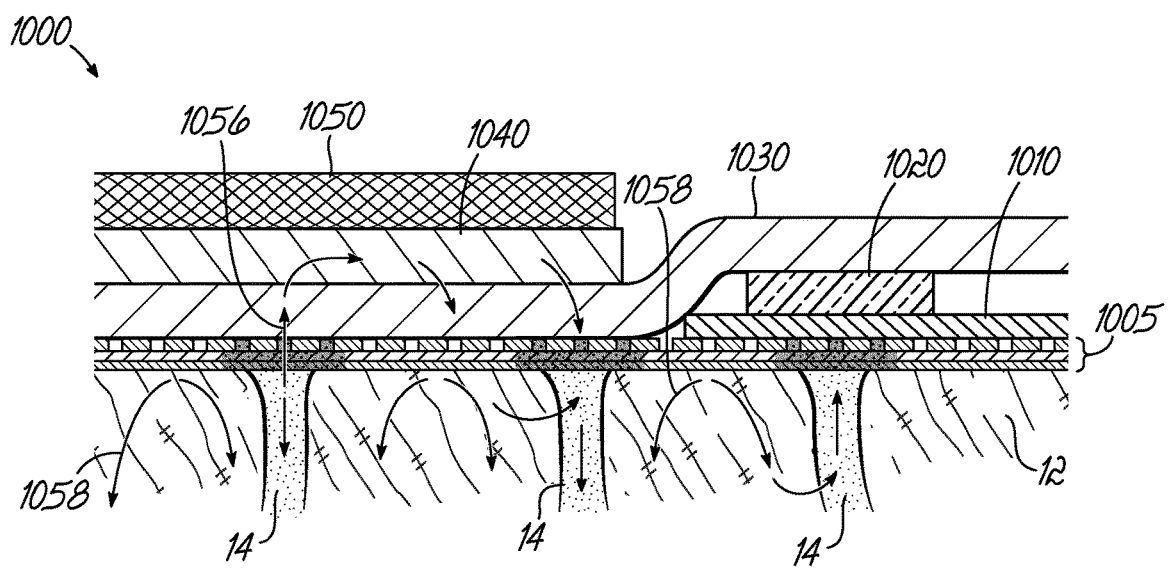
FIGS. 10 and 11 are cross-sectional views of at least a portion of devices according to various embodiments of the present invention that are capable of stimulating sweat.

With reference to FIG. 10, device 1000 includes a sensor 1020, a microfluidic component 1030, a substrate 1010, and a sweat stimulation mechanism. The sweat stimulation mechanism includes a sweat stimulation electrode 1050 and reservoir of sweat stimulant 1040. In the illustrated embodiment, sweat stimulation is limited or favored to regions only where element 1005 allows fluid or iontophoretic connection 1056 with sweat ducts 14. Element 1005 disfavors transport 1058. This advantageously localizes sweat stimulation and reduces potential adverse side-effects or irritation of prolonged sweat stimulation, or short term stimulation for persons with sensitive skin. Additionally, this would be of particular advantage for stimulating sweat, for instance, on the back of an individual, where sweat gland density is lower and a smaller fractional area of the skin would be stimulated and therefore potentially irritated. Thus, reduced sweat volume not only benefits sampling interval, but is of utility in sweat stimulation as well. Although not shown, sweat stimulation can also benefit from reduced sweat volume even if the sweat stimulation is indirect, such as is the case for sudo-motor axon reflex sweating. One embodiment of the present inventions includes sweat stimulation by means of a diffusing sweat stimulant (i.e., not requiring electric field for iontophoresis).

Figure 11:
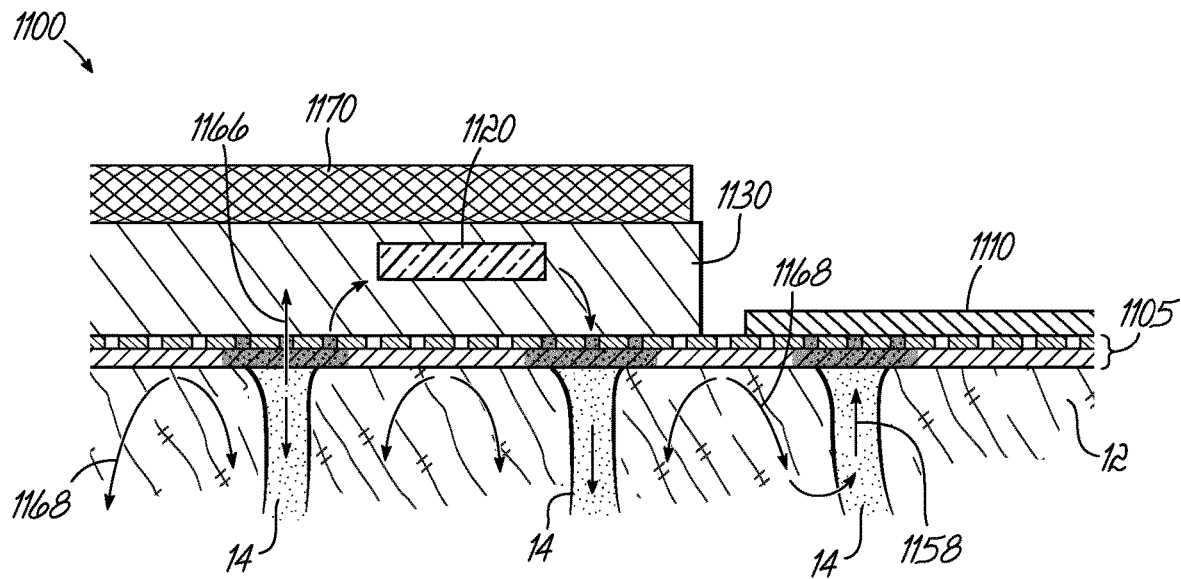

With reference to FIG. 11, device 1100 includes a sensor 1120 in a microfluidic component or gel 1130 and an electrode 1170, which is utilized to iontophoretically or electrosmotically extract solutes from the body from sweat ducts 14 (line 1166). The fluid or transport connection 1158 enabled by element 1105 that is favored above sweat ducts 14 allows solute extraction to be favored from sweat ducts 14, rather than transport 1168. In some cases, this could provide, for example, favored access to solutes in blood that are desired to be measured (e.g., sweat ducts in some cases provide a shorter or more conductive transport path between blood and the outside of the body). One of ordinary skill in the art would recognize that sweat stimulation and solute extraction illustrated in FIGS. 10 and 11 could also be combined and materials/layers arranged as needed to enable performance for a particular application. A substrate 1110 may, for instance, help provide physical stability to the device. In an aspect of the present invention, reduced sweat volumes are also advantageous to include solute flow or collection by diffusion, iontophoresis, or electrosmosis, and not just due to advective flow.

Figure 12:
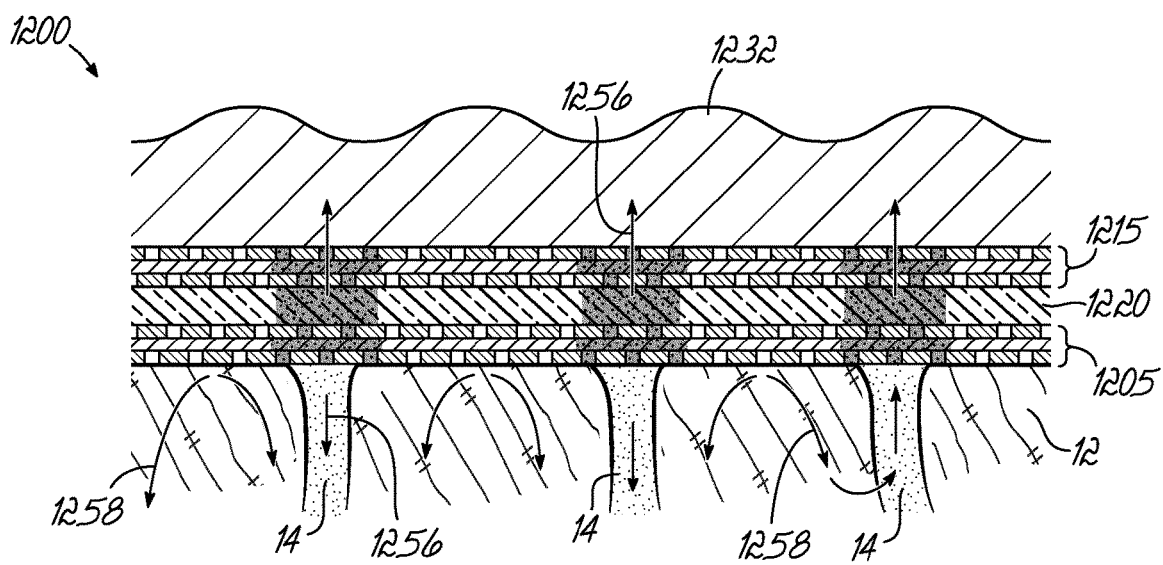
FIG. 12 is a cross-sectional view of at least a portion of a device according to one embodiment of the present invention.

With reference to FIG. 12, device 1200 includes a second element 1215, which may be similar in one or more functions to element 1205 (e.g., element 905 of FIG. 9 or other suitable methods as taught herein). Element 1215 is placed above sensor 1220 and is covered by a gel 1232. Device 1200, for example, could include an impedance spectroscopy sensor, or amperometric sensor, and sensor electrodes could be adjacent to or carried by elements 1205, 1215. Advantages of the device 1200 include the following: mitigation of the back-diffusion of solutes from gel 1232; mitigation of contamination by skin solutes; and substantial reduction of fluid volumes or flows needed. Some or all of these exemplary advantages could be highly favorable for sweat sensing applications, including those where minimal sweat stimulation is desired. In alternate embodiments, element 1205 may not be present, and sensor 1220 may be placed adjacent to the skin. In one embodiment, a thin adhesive may be between sensor and the skin.

Figure 13A:
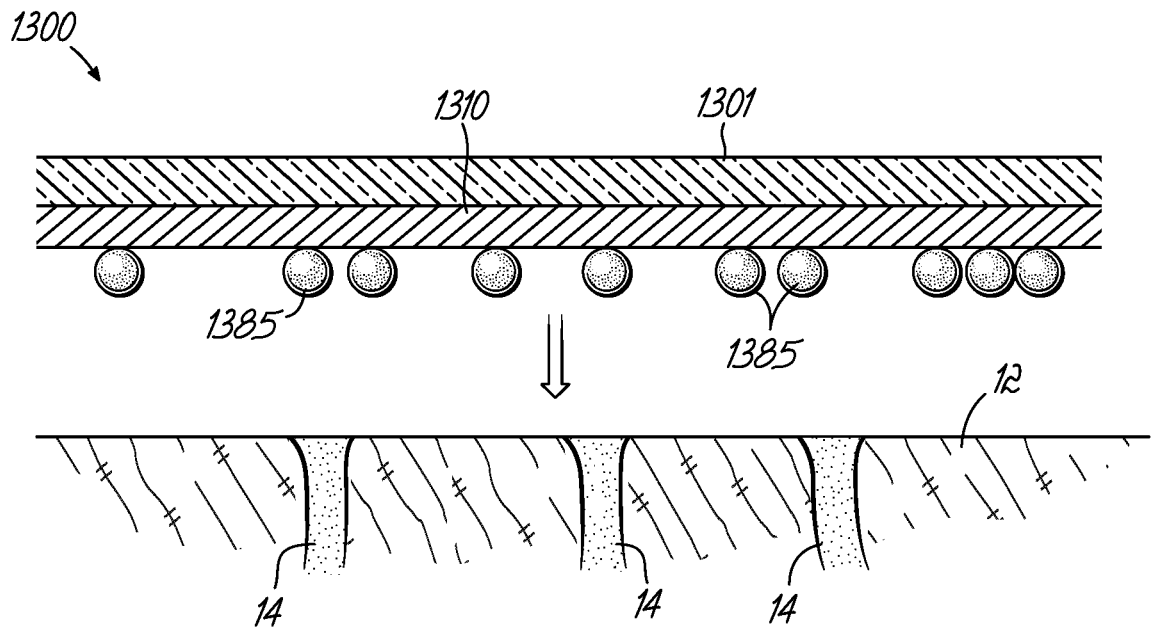
FIG. 13A is a cross-sectional view of a device according to one embodiment of the present invention
Figure 13B:
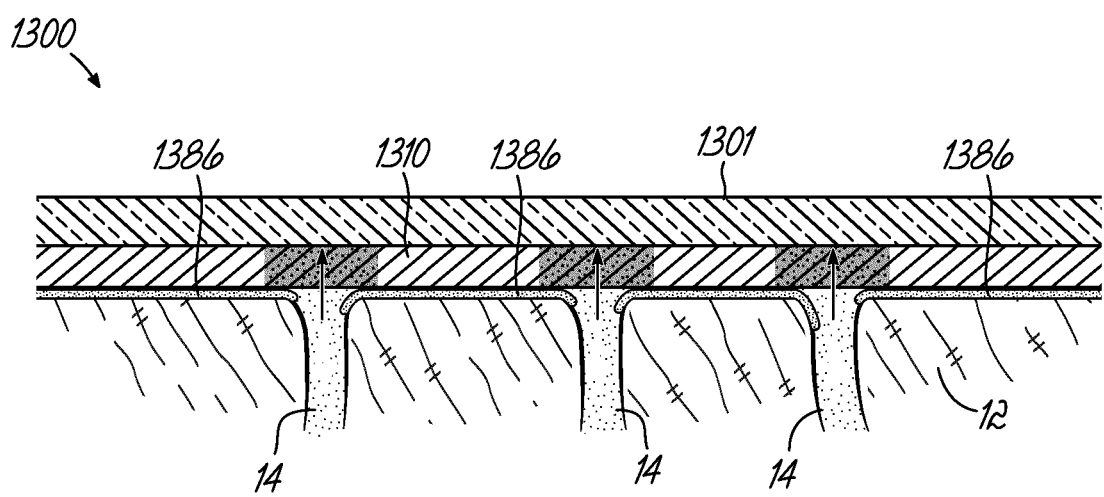
FIG. 13B is a cross-sectional view of the device of FIG. 13A after it has been placed on the skin.

With reference to FIG. 13A, a sweat sensing device 1300 includes an adhesive 1310 that includes a carrier, shown as burstable microcapsules 1385, which contain a barrier material. For convenience, element 1301 schematically represents various components of device 1300. In one embodiment, for example, element 1301 represents a sensor and a microfluidic component. The barrier material may be, for example, a solution of a barrier polymer in a suitable solvent. As the device 1300 is firmly applied to skin 12, the microcapsules 1385 burst and skin 12 is coated with the barrier material. In this regard, the barrier material and the carrier 1385 are a component of the device 1300 and are applied to the skin simultaneously with the other components of the device 1300. Element 1310 may be porous such that sweat may flow through element 1310 to be sensed by element 1301. The porosity or fluid pathway for sweat into the element 1310 could be maintained for example by having pores of similar diameter to that of sweat ducts 14 such that the pores are not sealed by the barrier polymer. The solvent in the barrier polymer dissipates over time into the skin 12 or the environment, resulting in a barrier film 1386 as shown in FIG. 13B. The barrier material could also be solvent-free, could be cured by a change in pH, or could be cured by the presence of oxygen or other stimuli or chemicals as the barrier material is applied to skin. The adhesive 1310 could contain, or carry on its surface, additional microcapsules of a curing agent or other material that, when crushed or burst, causes the barrier material to cure. Adhesives that are initially microencapsulated could also be used in combination with other aspects of the present invention.

In another embodiment, the barrier material could be a solid dry film or material on top of adhesive 1310. The skin 12 may be prepared and cleaned with a solvent, which cleans skin and is a solvent for barrier material. The device 1300 is then placed onto skin 12 where barrier material comes into contact with the solvent causing the barrier material to dissolve and coat the skin surface. The barrier material film 1386 dries as the solvent dissipates into skin 12 or the environment, resulting in a configuration similar to that shown in FIG. 13B. Numerous alcohols are used in skin cleaning, and those with lower vapor pressures could be utilized, which would keep the solvent in or on skin during patch application.

In another aspect of the present invention, devices may also include selective transport elements that transport only a solute of interest, such as Ammonia, for example. An exemplary embodiment may use an Ammonia ionophore doped polymer layer. In this case, the selective nature of the transport element would prevent solutes other than Ammonia coming from skin that could reduce the performance of sensors.

In another aspect of the present invention, the adhesives could also alter properties of the top layer of skin such that the skin itself becomes less prone to transport of solutes. Only in areas where the adhesive touches skin would this occur, which therefore precludes alteration of transport where there is no skin (e.g. the opening of a sweat duct). In one embodiment, an adhesive could have a phase that is a very low molecular weight sealing polymer in a solvent that penetrates into skin and seals it substantially except above sweat ducts. Examples of such adhesives include, without limitation, barrier polymer formulations similar to that of Smith and Nephew SKIN-PREP product, and are also provided by Lutz of 3M Corp in "Performance Assessment of Film Forming Barriers (Skin Sealants)", included herein by reference.

Figure 14:
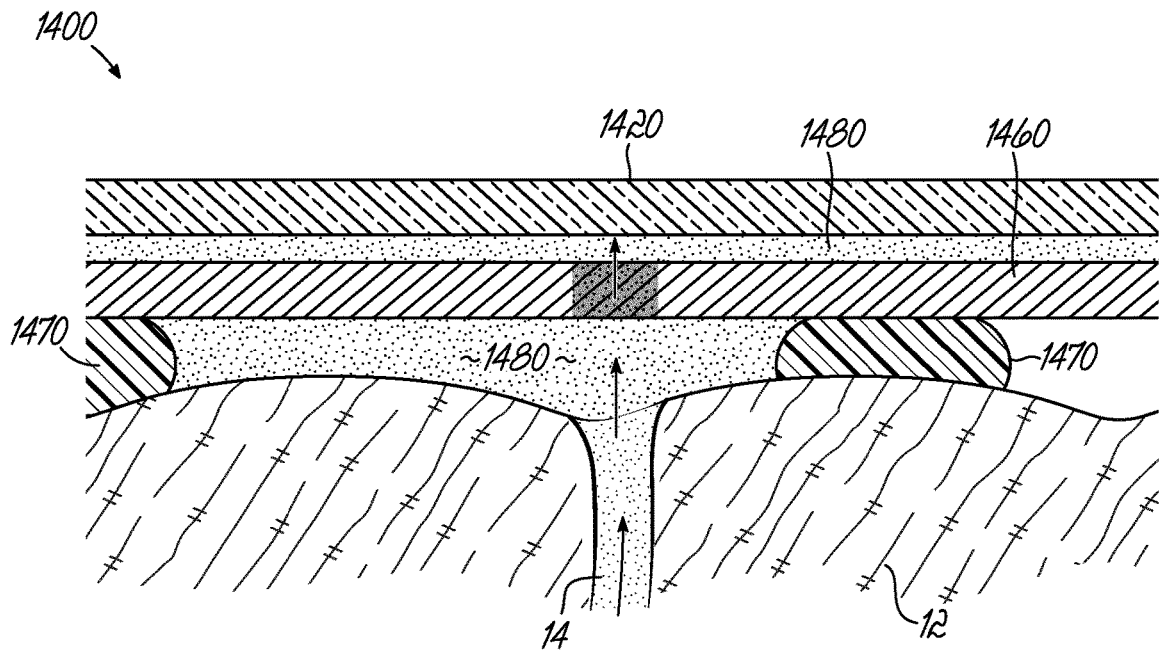
FIGS. 14 and 15 are cross-sectional views of devices according to various embodiments of the present invention.

With reference to FIG. 14, a device 1400 includes an adhesive 1470 and a pressure-permeated component 1460 that together produce a reduced volume pathway 1480. The adhesive 1470, for example, could be in a hexagonal or other closed-cell pattern, as previously discussed. Regarding structure and composition, such a configuration can also be referred to as having a dominantly vertical porous network. The sensor 1420 would therefore receive sweat more quickly than otherwise due to the volume reduced pathway 1480. The volume reduced pathway 1480 could be combined with other aspects of the present invention to further reduce the sweat volume for the device 1400.

Figure 15:
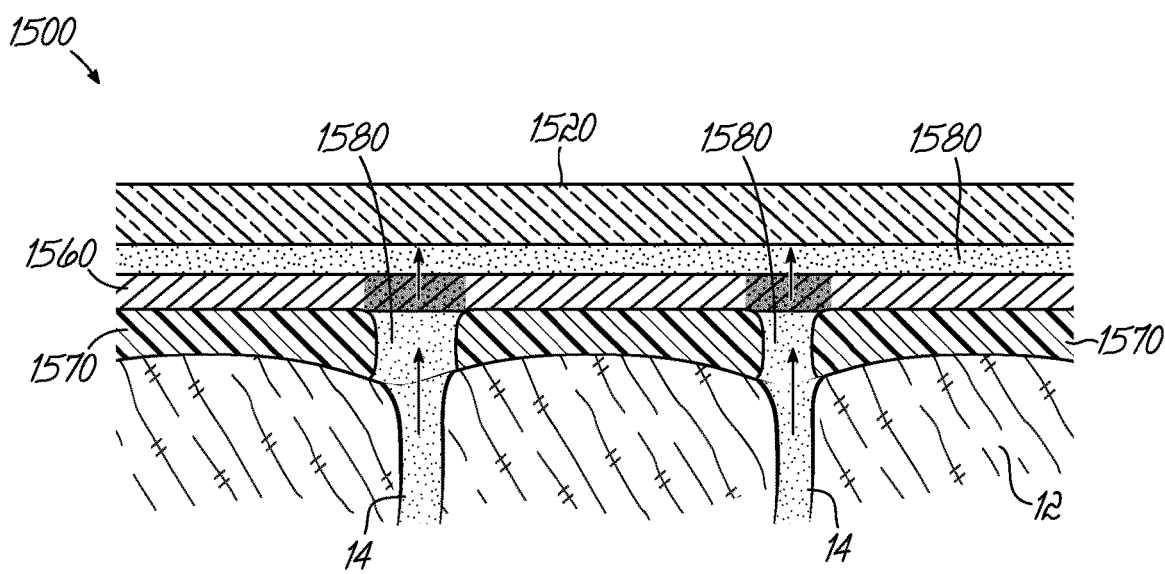

With reference to FIG. 15, a device 1500 a sensor 1520 and further includes a material 1570 and an optional pressure permeated component 1560 that create a reduced volume pathway 1580 by allowing a more rapid flow of sweat vertically away from skin as compared to flow of sweat horizontally (i.e., parallel with the surface of skin). Pressure-permeated component 1560 may be present in embodiments of the present invention where the material 1570 itself is unable to suitably reduce the sweat volume. In one embodiment, material 1570 is an adhesive.

In an alternate embodiment of device 1500, the optional pressure permeated component is not included. In such an embodiment, most of the material comprising the adhesive could be significantly sweat impermeable, and the adhesive is fitted with tubes, pores, or micro-fibers, which are porous to sweat and the provided flow path is dominantly vertical. In other words, the adhesive would have a vertically anisotropic sweat pathway (i.e., the adhesive favors vertical transport of sweat or solutes in sweat over horizontal transport), which could also be referred to as a dominantly vertical porous network. Such an adhesive could be made, for example, by forming a thick adhesive with flexible tubes, pores, or micro-fibers that are vertically oriented and then slicing the adhesive into thinner layers. The slicing would substantially expose the tubes or pores on either side of the adhesive. Alternately, an adhesive could be made with porous or dissolvable particles that form vertical pores. For example, a phase separation could occur during curing of the adhesive, the first phase being the adhesive and the second phase being a volatile fluid where the volatile fluid forms dominantly vertically-oriented pores as it escapes the adhesive during curing. Pores could also be mechanically created, for example with microneedles that punch through the adhesive to create pores before said adhesive is used on skin. Alternately, pores or wicking fibers could be randomly oriented in the adhesive and be of a length comparable to the thickness of the adhesive, such that some will provide a vertically porous pathway whereas those that are horizontal will not because they terminate substantially inside an adhesive that is substantially sweat impermeable. The density of vertical pathways for sweat should be greater than the density of sweat ducts such that the above stated benefits are realized and an adequate amount of sweat reaches the device to be sensed.

Adhesives useful in embodiments of the present invention may have a variety of formulations. By way of example, an adhesive could be a hydrogel, an acrylate, a hydrocolloid, or a type of medical adhesive. Numerous adhesive formulations can be adapted using components and chemistries for hydrocolloid dressings and adhesives, which can be optimized to be highly porous or highly non-porous to sweat, gas, microbes, oils, etc. Such adhesives can be utilized also with antimicrobial, oil-absorbing beads, pH buffering or maintaining beads, or other substances that would improve the long-term reliability and wearability of a sweat sensing device. The adhesive may also be electrically conductive by itself or by virtue of containing sweat such that it can be used for solute transport in sampling solutes or in iontophoretic delivery with a device of the present invention.

Adhesives or other materials that are vertically anisotropic in sweat flow that are useful in embodiments of the present invention may have a variety of configurations. By way of example, an adhesive may include filaments or pores that have a dominantly vertical path, such filaments or pores being porous and/or soluble in sweat. In one embodiment, a vertical fiber array made of water soluble polyvinylpyrrolidone could be made by creating a structure similar to Velcro using water soluble polyvinylpyrrolidone as the polymer. This Velcro-like surface could then be embedded with adhesive or gels that are significantly sweat impermeable. When the device is placed on the skin, the sweat would dissolve the polyvinylpyrrolidone forming a reduced volume pathway for the sweat.

In an aspect of the present invention, reduced sweat volumes may improve the sweat sampling rate. In some cases, applying a device using methods like a bandage is inadequate to minimize the sweat volume. In fact, few wearable technologies require the reduced volume like the sweat volume of the present invention, and therefore such need is completely or significantly unique to the present invention. The device could stay clamped to skin with pressure to reduce sweat volume, but in a simple patch or other wearable device there are other ways to minimize the sweat volume. In one aspect of the present invention, adhesives may be curable. A device having a curable adhesive is applied to skin along with external pressure sufficient to press the device against skin. The external pressure may be provided by, for example, a clamp, a rubber strap, or another apparatus. The adhesive could then cure such that it is able to retain most if not all of the reduced sweat volume created by the applied external pressure after the external pressure is removed. In this manner, the reduced sweat volume would improve the sweat sampling rate. The apparatus used to apply the devices could also contain elements to deliver the curing stimulus (e.g. a heating element, or a UV LED array). A catalyst could be soaked into skin before applying the device also, the device applied, and the catalyst causing the adhesive to cure while pressure is maintained long enough to support proper curing. In one embodiment, the adhesive itself could contain microcapsules of a curing agent or other material that when crushed or burst causes adhesive to cure.

A variety of curable adhesives are useful in embodiments of the present invention. Adhesives can be cured by at least one of optical, thermal, pH, a catalyst, a substance in or on skin, or other means such as solvent partitioning from adhesive in the liquid or gel state into dry skin. Curable adhesives may be used in combination with other aspects of the present invention. In one embodiment, adhesives could include beads or particles which would reduce the sweat volume inside the adhesive.

Figure 16:
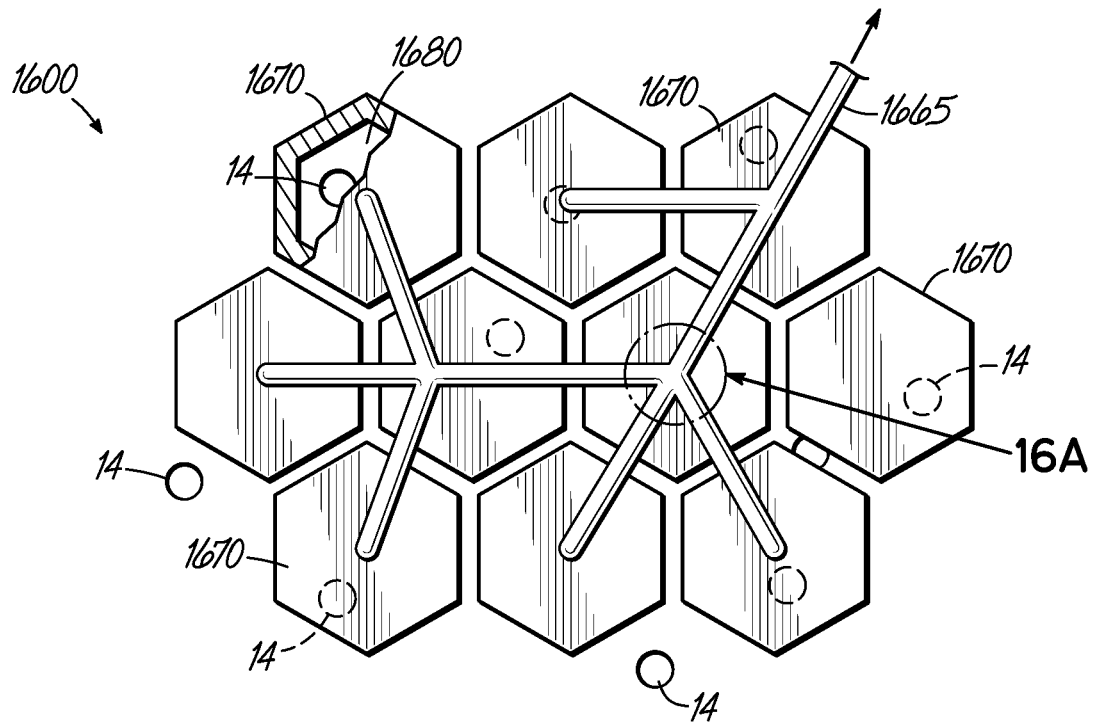
FIG. 16 is a top view of at least a portion of a device according to one embodiment of the present invention.
Figure 16A:
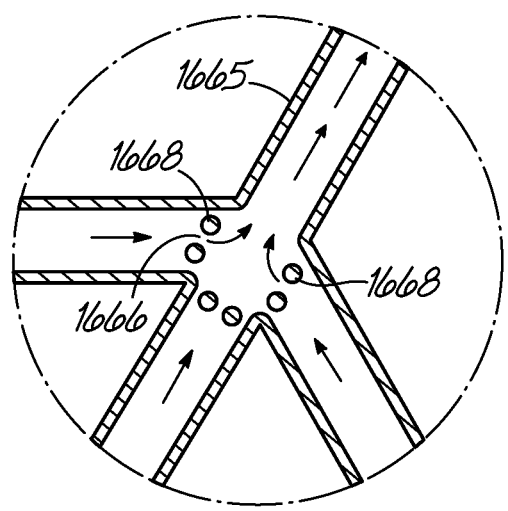
FIG. 16A is an enlarged view of the encircled portion 16A of the device of FIG. 16.

FIG. 16 shows a top view diagram of at least a portion of device 1600 of an embodiment of the present invention. Adhesive 1670 creates a volume-reduced pathway by creating a plurality of enclosed volumes 1680 as discussed above. When device 1600 is placed on the skin 12, some enclosed volumes 1680 will be aligned over sweat ducts 14, while others are not. Enclosed volumes 1680 over a sweat duct 14 would form a volume-reduced pathway for sweat. Alternatively, enclosed volumes 1680 not over a sweat duct 14 will not be a part of the volume-reduced pathway for sweat. Device 1600 also includes a microfluidic component 1665 to allow sweat collection from any of the enclosed volumes 1680 that might provide sweat. In this regard, the microfluidically connected network of closed-cells volumes provides a reduced sweat volume and reduced sweat pathway in device 1600. The microfluidic component 1665 could be any microfluidic pathway or material to transport sweat from enclosed volumes 1680 to one or more sensors (not shown) in the direction of the arrows shown. To further isolate each enclosed volume 1680 from each other, branches of the microfluidic component may include one-way or pressure-permeated flow values towards the sensors formed by, for example, pressure permeated points. Numerous one-way or pressure-permeated flow valves are known by those skilled in the art. In the illustrated embodiment in FIG. 16A, a one-way flow valve that is pressure permeated is used of posts or obstructions 1668 in the microfluidic component 1665 which result in a reduced diameter for sweat pressure permeation 1666 compared to the diameter for sweat flow without such posts or obstructions 1668 (i.e., obstructions 1668 behave like a pressure permeated component). While the microfluidic component 1665 is specifically shown as including obstructions 1668, it will be readily appreciated that in alternate embodiments, such a barrier may not be included. In one embodiment, the diffusion of sweat solutes along the branches of the microfluidic components may be low enough such that, even if all the enclosures fill with sweat, the sweat volume is reduced.

Figure 17:
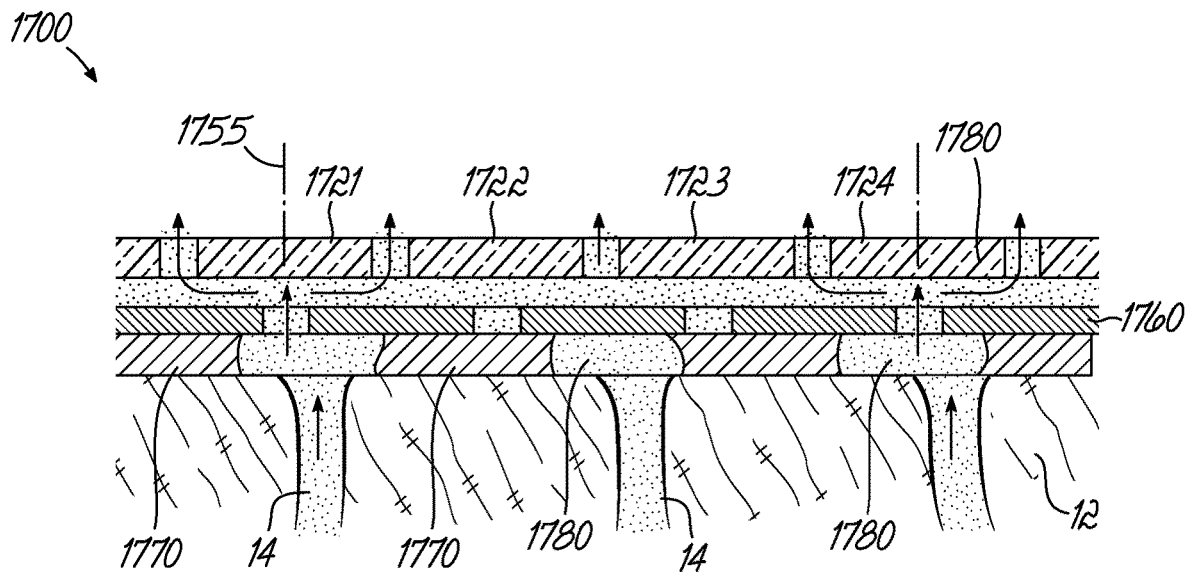
FIG. 17 is a cross-sectional view of a device according to one embodiment of the present invention.

With reference to FIG. 17, the device 1700 includes a set of sensors 1721, 1722, 1723, 1724, volume reducing component 1770, membrane or mesh 1760, and a volume reduced pathway 1780. Though not shown, a sweat stimulation element, such as sweat stimulating gel and driving electrode, may be further included. As indicated by line 1755, at least one sensor 1724 may have a sensor-centered volume reduced pathway 1780 for sweat coming from skin 12 and sweat duct 14, which decreases the sampling interval. Having a sensor-centered volume reduced pathway is advantageous because, if sweat flow is not centered, then a portion of the sensor will have non-uniform and much slower flow. In particular, a flow of sweat near at least a first region would be slower than the flow at other regions under the sensor. This slow sweat flow will cause old sweat to be measured along with new sweat, which will effectively increase the sampling interval. Thus, a sensor placed on skin 12, however small, or however much the sweat volume is reduced between the sensor and sweat ducts, could receive a flow of sweat that is not centered under the sensing surface of the sensor. The present invention contemplates numerous methods of achieving a sensor-centered volume reduced pathway, such as pathway 1780. For a sensor having a circular area, flow into the center of the sensor would be optimal in terms of minimizing mixing of simultaneous readings of old sweat and new sweat. While the term 'centered' may not exactly apply to sensors with non-circular geometries, aspects of the present invention include a sensor configuration that receives sweat in a manner that results in an optimum or near optimum sampling interval. For example, in one embodiment of the present invention, a device may include at least one sensor and at least one volume reduced pathway, where the volume reduced pathway has a flow pattern for a fast sampling interval for the sensor. In other words, the volume-reduced pathway includes a predetermined pathway across sensors for sweat, which decreases the sampling interval. It should be recognized that device 1700 and similar embodiments may be constructed using a variety of methods. By way of example, device 1700 may be constructed using aligned lamination of films or photolithography, among other methods.

In one advantageous aspect of the present invention, a sensor may be porous to sweat. Including a sensor porous to sweat may reduce the time needed for new sweat to flush old sweat away from sensors. Additionally, if the sensor is porous, then the flow of sweat would be centered or uniform through the sensor (hence 'centered flow' may also include 'uniform flow'). Porous sensors may also extend benefits to other embodiments of the present invention even without having centered or uniform flow.

Figure 17A:
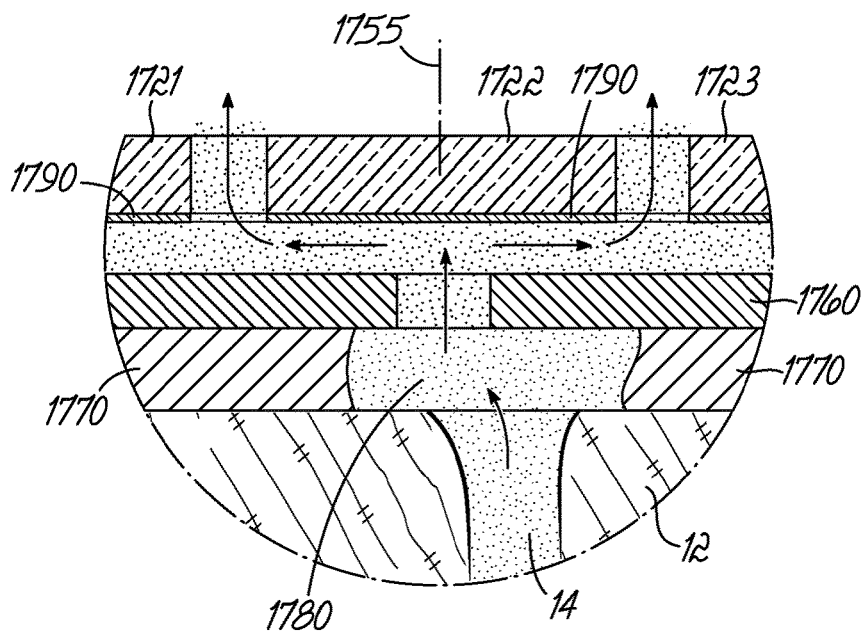
FIG. 17A is an enlarged view of a portion of the device of FIG. 17.

In one aspect of the present invention, a sensor may be coated with a sweat-wetting material to improve the wettability of sweat to the sensor. Some sensors are hydrophobic, or at least not adequately hydrophilic, on their surface to be uniformly wetted by sweat. Conventionally, a textile, paper, or microfluidic component or feature could be placed adjacent to a sensor to wick and wet fluid against the sensor surface. However, any such additional component increases the sweat volume substantially, especially considering the thickness of textiles or paper components. With respect to FIG. 17A, in one embodiment of the present invention, the surfaces of the sensors 1721, 1722, 1723 facing the skin 12 are coated with a hydrophilic or super-hydrophilic coating 1790. The sensor coating may be, for example, polyvinylpyrrolidone, wicking nano-fibers, or other materials placed directly onto the sensor surface. By way of example, the sensor coating could be spray coated using a dilute solution in water, ethanol, with or without surfactants to improve coating wetting to the sensor surface. In dry form, such coatings could range from several mono-layers thick to microns thick or greater and still achieve the desired wetting of sweat across the sensor surface. The sweat-wetting coating on the sensor provides a reduced sweat volume or volume-reduced pathway compared to conventional methods.

With reference to embodiments of the present invention, adhesives, bead layers, or other features or materials have been illustrated for contact on skin without particles, hairs, moles, or other features on skin that would increase sweat volume. The present invention includes alterations of the embodiments to cover such issues as well, such as skin smoothing or including device modifications such as thicker layers or adhesives.

The following examples are provided to help illustrate the present invention, and are not comprehensive or limiting in any manner.

Example 1

Low sweat rates or targeted solute extraction regions enabled by the present invention can also allow sensing of some solutes that otherwise might be difficult. For example, a large sweat rate can cause the sweat gland itself to generate significant lactate, and make measurement of blood lactate not possible. The embodiments of the present invention could allow blood lactate that partitions into sweat ducts or glands to be dominant over lactate generated by the sweat gland, and therefore enable improved measurement of lactate through sweat ducts or glands. Similarly, larger size or lipophilic sweat solutes may diffuse into sweat very slowly, and require sampling at very low sweat rates to provide correlation to blood, and therefore the reduced sweat volumes of the present invention are of significant value. This example further illustrates that sweat volumes of the present invention are of value beyond just sampling interval.

Example 2

Calculations were performed to determine the sampling interval for a sweat sensing device on an example sweat sampling site of 140 glands/cm$^2$ (e.g., the abdomen) and a sweat generation rate of 0.5 and 5 nL per minute. Using a simple volume fill model, a 2.5 mm diameter sensor with an average gap from the skin surface of 30 μm would provide a sampling interval of 42.9 and 4.3 minutes for 5 and 0.5 nL/min/gland, respectively. This example has no reduced sweat volume.

Example 3

Using the same sampling site characteristics and sensor size, an example was calculated where petroleum jelly is filling the sweat volume between the sensor and the skin. Negligible sweat volume between the sensor and the petroleum jelly is assumed (e.g., a pressure permeated component may be between the sensor and the petroleum jelly). The resulting sampling interval at 0.5 nL/min/gland is less than one minute. Even having a space as little as 10 μm between the sensor and the pressure permeated component, a 3 times improvement in sampling interval is provided over example 2.

Example 4

Using the same sampling site characteristics and sensor size, an example was calculated where the device includes a hexagonal closed-cell lattice of adhesive on skin. Assuming the adhesive height is 30 μm and the adhesive width is 3:1 aspect ratio (i.e., width of 90 μm), the adhesive diameter for 80% open area would be 360 μm. The resulting sampling interval at 0.5 nL/min/gland is less than four minutes. In this regard, even if space exists between the sensor and the pressure permeated component, at least a portion of the sweat volume has been substantially reduced.

Example 5

Using the same sampling site characteristics and sensor size as Example 4, an example was calculated where the device includes randomly packed hydrophobic beads. The resulting sampling interval at 0.5 nL/min/gland is less than one minute. In this regard, even if space exists between the sensor and the pressure permeated component, at least a portion of the sweat volume has been substantially reduced.

What is claimed is:

1. A sweat sensor device for sensing sweat on the skin comprising:
   one or more sweat sensors; and
   a volume-reducing component that provides a dominantly vertical pathway for sweat between and sweat glands and the one or more sweat sensors when said device is positioned on said skin,
   wherein said volume-reducing component is selected from the group consisting of a volume-reducing material and a pressure-permeated component, a sweat dissolvable material, a mechanically compliant material for conforming to a surface of said skin, an adhesive with a vertically anisotropic sweat pathway, the adhesive preventing horizontal movement of sweat, microcapsules including a barrier material, and combinations thereof.

2. The device of claim 1, wherein the volume-reducing component includes a material configured to dissolve on contact with sweat so that sweat creates one or more vertical pathways from the skin through the material, and a pressure-permeated component.

3. The device of claim 1, wherein the volume-reducing component includes a plurality of pathways oriented vertically, and wherein the pathways are configured to inhibit horizontal movement of sweat.

4. The device of claim 3, wherein the plurality of enclosed volumes is a microfluidically connected network of closed-cell sweat volumes.

5. The device of claim 1, wherein the volume-reducing component includes a curable adhesive.

6. The device of claim 1, wherein the volume-reducing component includes a sweat dissolvable material that is configured to dissolve on contact with sweat so that sweat creates one or more vertical pathways from the skin through the material.

7. The device of claim 6, wherein the sweat dissolvable material is microporous.

8. The device of claim 6, wherein the sweat dissolvable material includes a sweat-wetting promoting feature.

9. The device of claim 1, wherein the volume-reducing component includes the mechanically compliant material for conforming to a surface of said skin, the mechanically compliant material including a plurality of beads.

10. The device of claim 9, wherein at least a portion of the beads are hydrophilic.

11. The device of claim 9, wherein at least a portion of the beads are hydrophobic.

12. The device of claim 9, wherein at least a portion of the beads are oleoscopic.

13. The device of claim 9, wherein at least a portion of the beads include a transferable sweat impermeable coating.

14. The device of claim 9, wherein at least a portion of the beads include an adhesive coating.

15. The device of claim 9, wherein at least a portion of the beads have at least one magnetic property.

16. The device of claim 1, wherein the volume-reducing component includes an adhesive with a vertically anisotropic sweat pathway.

17. The device of claim 16, wherein said adhesive includes a dominantly vertical porous network.

18. The device of claim 1, wherein the volume-reducing component includes microcapsules including a barrier material and, when the device is applied to the skin, the microcapsules release the barrier material to form a barrier on said skin.

19. The device of claim 1, including a sweat stimulating component.

20. The device of claim 19, wherein said sweat stimulation component includes a second volume-reduced pathway between sweat stimulating component and sweat glands when said device is positioned on said skin; and
wherein said volume-reducing pathway is defined by one or more features from the group consisting of a volume-reducing material and a pressure-permeated component, a sweat dissolvable material, a mechanically compliant material for conforming to a surface of said skin, an adhesive with a vertically anisotropic sweat pathway, microcapsules including a barrier material, beads, a plurality of horizontally enclosed volumes, and combinations thereof.

21. The device of claim 1, wherein said volume reducing component provides a volume-reduced pathway for sweat between said one or more sweat sensors and sweat glands when said device is positioned on said skin, said volume-reduced pathway including a predetermined pathway for sweat across said sensors; and
wherein one or more sensors has a sampling interval when sensing sweat and said volume reduced pathway decreases the sampling interval for said one or more sensors.

22. The device of claim 21, wherein a flow of said sweat from said skin is centered in said one or more sweat sensors.

23. A sweat sensor device for sensing sweat on the skin comprising:
one or more sweat sensors; and
a volume-reducing component that provides a volume-reduced pathway for sweat between the one or more sweat sensors and sweat glands when said device is positioned on said skin,
wherein said volume-reducing component includes a plurality of enclosed volumes.

24. The device of claim 23, wherein said plurality of enclosed volumes is a microfluidically connected network of closed-cell sweat volumes.

* * * * *

UNITED STATES PATENT AND TRADEMARK OFFICE
CERTIFICATE OF CORRECTION

PATENT NO. : 10,639,015 B2
APPLICATION NO. : 15/314418
DATED : May 5, 2020
INVENTOR(S) : Jason C. Heikenfeld Page 1 of 1

It is certified that error appears in the above-identified patent and that said Letters Patent is hereby corrected as shown below:

In the Claims

Column 24, Line 10 (Claim 1), "for sweat between and sweat glands" should be --for sweat between sweat glands--.

Signed and Sealed this
Fourth Day of August, 2020

Andrei Iancu
*Director of the United States Patent and Trademark Office*